(12) United States Patent
Yamamoto et al.

(10) Patent No.: US 7,205,149 B2
(45) Date of Patent: Apr. 17, 2007

(54) GENE OF ENZYME REACTIVATING DNA DAMAGED BY ULTRAVIOLET LIGHT USING VISIBLE LIGHT

(75) Inventors: Kazuo Yamamoto, Sendai (JP); Tadashi Kumagai, Sendai (JP); Jun Hidema, Sendai (JP); Atsuhisa Hirouchi, Sendai (JP)

(73) Assignee: Japan Science and Technology Agency, Saitama (JP)

( * ) Notice: Subject to any disclaimer, the term of this patent is extended or adjusted under 35 U.S.C. 154(b) by 81 days.

(21) Appl. No.: 10/492,904

(22) PCT Filed: Oct. 11, 2002

(86) PCT No.: PCT/JP02/10568

§ 371 (c)(1),
(2), (4) Date: Apr. 16, 2004

(87) PCT Pub. No.: WO03/033704

PCT Pub. Date: Apr. 24, 2003

(65) Prior Publication Data

US 2005/0074766 A1    Apr. 7, 2005

(30) Foreign Application Priority Data

Oct. 18, 2001 (JP) .............................. 2001-320138

(51) Int. Cl.
*A01H 5/00* (2006.01)
*C12N 15/82* (2006.01)
*C12N 15/29* (2006.01)
*C07H 21/00* (2006.01)

(52) U.S. Cl. ................... 435/468; 435/320.1; 435/488; 536/23.6

(58) Field of Classification Search ..................... None
See application file for complete search history.

(56) References Cited

OTHER PUBLICATIONS

Theologis et al. (NCBI, GenBANK, Accession No. AE005172, pp. 1-3, Published Dec. 14, 2001).*
Keshin et al. (Protein Science, 13:1043-1055, 2004).*
Guo et al. (PNAS, 101:9205-9210, 2004).*
Thornton et al. (Nature structural Biology, structural genomics supplement, Nov. 2000).*
Database Embl., Oct. 1, 2002, Wing R.A. et al., "Putative CPD Photolyase", XP002296394, Database accession No. Q8LM09.
Hirouchi et al., Molecular Genetics and Genomics, vol. 269, No. 4, pp. 508-516, 2003.
M. Ahmad et al., *The Plant Cell*, vol. 9, pp. 199-207 (1997).
S. Nakajima et al., *Nucleic Acids Research*, vol. 26, No. 2, pp. 638-644 (1998).
T. Kato Jr. et al., *Nucleic Acids Research*, vol. 22, No. 20, pp. 4119-4124 (1994).
A. Yasui et al., *The EMBO Journal*, vol. 13, No. 24, pp. 6143-6151 (1994).
J. Peterson et al., *Plant Molecular Biology*, vol. 40, pp. 1063-1071 (1999).
J. Hidema et al., *The Plant Cell*, vol. 12, pp. 1569-1578 (2000).
J. Hidema et al., *Plant Physiol.*, vol. 113, pp. 39-44 (1997).
H. Kang et al., *Photochemistry an Photobiology*, vol. 68, No. 1, pp. 71-77 (1998).
A. Sancar, "Structure and Function of DNA Photolyase", Biochem., vol. 33, No. 1, pp. 2-9 (1994).
Todo et al., "A new photoreactivating enzyme that specifically repairs ultraviolet light-induced (6-4)photoproducts", Nature, vol. 361, pp. 371-374 (1993).
G. Ries et al., "Elevated UV-B radiation reduces genome stability in plants", Nature, vol. 406, pp. 98-101 (2000).
Y. Liu et al., "Development of an efficient maintenance and screening system for large-insert genomic DNA libraries of hexaploid wheat in a trasformation-competent artificial chromosome (TAC) vector", The Plant Journ., vol. 23, No. 5, pp. 687-695 (2000).
K. Maruyama et al., "Oligo-capping: a simple method to replace the cap structure of eukaryotic mRNAs with oligoribonucleotides", Gene, vol. 138, pp. 171-174 (1994).
M. Herrier, "Use of SMART-generated cDNA for Differential Gene Expression Studies", J. Mol. Med., vol. 78, pp. B23 (2000).
A. Sancar, "No 'End of History' for Photolyases", Science, vol. 272, pp. 48-49 (1996).

* cited by examiner

*Primary Examiner*—Ashwin Mehta
*Assistant Examiner*—Vinod Kumar
(74) *Attorney, Agent, or Firm*—Peter F. Corless; Christine C. O'Day; Edwards Angell Palmer & Dodge LLP

(57) ABSTRACT

It is intended to contribute to the solution of environmental problems caused by destroying the ozone layer and serious problems concerning the food resources in the 21st century by isolating a photoreactivating enzyme from an ultraviolet light-tolerant rice plant, thus acquiring information on the photoreactivation mechanism of the plant which still remains unknown mostly, and constructing an ultraviolet light-tolerant plant with the use of a cloned gene. Genes encoding a photoreactivating enzyme originating in rice plant, in particular, a gene encoding a protein as specified in the following (a) or (b): (a) a protein comprising the amino acid sequence represented by SEQ ID NO:1; and (b) a protein comprising an amino acid sequence derived from the amino acid sequence (a) by deletion, substitution or addition of one to several amino acids and having a photoreactivating enzyme activity.

9 Claims, 10 Drawing Sheets

FIG.2

```
                 1         15 16            30 31            45 46            60 61            75 76              90
1 A.t   ---------------   ---------------   ---MASTVSV       QPGRIRILKKGSWQP  SDQTVGPVVYTMFRD  QRLKDNMALIHAVDL    52
2 C.r   MSSKRKATEAPAAGE   DGAAGPSSKKQAAAS   ASAAAAAAGAGSAAA  GGALVNPKRVRVLKP  GSIGKGPVVYTMSRD  QRLADNMALHAIEA     90
                                                                                              AC1

91        105 106           120 121          135 136          150 151          165 166            180
1 A.t   AN--RTNAPVAVVFN   LFDQFLDAKARQLGF   MLKGLRQLHHQIDSL  QIPFFLEQGDAKETI  PNFLTECGASHLVTD  FSPLREIRRCKDEVV   140
2 C.r   AQGAAGSSQVAVAFN   LVPAFLGAGAROFGF   MLRGLRQLAPRLEAR  GIKFYLLKGDPAHTL  PQLVSGLGAGLLVTD  YSBLRLGRTWRDQVC   180

181       195 196           210 211          225 226          240 241          255 256            270
1 A.t   KRTSDSLAIHEVDAH   NVVPMWAABSKLEYS   ARTIRGKINKLLPDY  LIEFPKLEPPKKKWT  GMMDKKLVDMDSLID  KVVREGAEVPEIEMC   230
2 C.r   S-ALGSVPHEVDAH    NVVPVWAASEKREVG   ARTLRPKIHKALPEF  LREFPEVP-TLPAWT  PAVAPEAVDMDGLIS  EVLSRGADVPEVEMC   268
                         AC2

271       285 286           300 301          315 316          330 331          345 346            360
1 A.t   VRQEDAGIEVIMCNK   DGFLITKRLKNYSTDR  NNPIKPKALSCLSPY  LHFCQVSAQRCALEA  RKVRSTSPQAVDIFL  EELIVRRELSDNFCY   320
2 C.r   TPGEAALEAITGPR    GFLSPARLSLYDTKR   NDPATPSALSGLSPY  LHFCQLAPQRAALEA  AKHRAKYKAAVESYL  EELVVRRELADNFCH   358
                                                            AC3

361       375 376           390 391          405 406          420 421          435 436            450
1 A.t   YQFHYDSLKGAWEMA   RKSTMDHASDKREHI   YSLEQIEKGLTADPL  WNASQLEMLYQGKMH  GFWRLVYMAKKILEMT  KGPEEALSISIYLNN   410
2 C.r   YCFTYDSLEAAAEMA   RDSLDKHRTDKREFL   YTRDQLECGATHDEL  WNAAQLEMVHVGKMH  GFWRLVYMAKKILEMT  QGPEQAIEWAIYLND   448
                                                            AC4

451       465 466           480 481          495 496          510 511          525 526            540
1 A.t   KYEIDGRDPSGYVGC   MWSICGVHDQGWKER   PVFGKIRYMNYAGCK  RKFNVDSYISVVKSL  VSVTKKRKAEEQLT   RDSVDPKITIV----   496
2 C.r   RYELDGRDPGGYTCV   LWSMAGVHDMGWAER   AVFGKIRYMNYNGCK  RKFDIKAYVAYVSKA  VAEAKARGRAAKLPS  AAAAGASGAAAAGAT   538
                                                            AC5

541       555 556           570 571          585 586          600 601          615 616            630
1 A.t   ---------------   ---------------   ---------------  ---------------  ---------------  ---------------
2 C.r   AAAAAAAAPGPSGAQ   AAKAAKAAKAEPKEAK  PKAAKAAAKAKGPKD  EKAAAAGAKRKAAKP  AKSASSGEEGSDDE                     612
```

| Hs | : *Homo sapiens* |
| Dm | : *Drosophila melanogaster* |
| Xl | : *Xenopus laevis* |
| At | : *Arabidopsis thaliana* |
| Cr | : *Chlamydomonas reinhardtii* |
| Hh | : *Halobacterium halobium* |
| An | : *Anacystis nidurans* |
| Ec | : *Escherichia coli* |
| Nc | : *Neurospora crassa* |
| Pt | : *Potorous tridactyls* |
| Ol | : *Oryzas latipes* |
| Mx | : *Myxococcus xanthus* |

| Lane.No. | primer | Lane.No. | primer | Lane.No. | |
|---|---|---|---|---|---|
| 1. | AC 1-2 | 6. | AC 2-4 | 11. | marker |
| 2. | AC 1-3 | 7. | AC 2-5 | | (from above 23, 9.6, 6.6, |
| 3. | AC 1-4 | 8. | AC 3-4 | | 4.4, 2.3, 2.0, 0.56kbp) |
| 4. | AC 1-5 | 9. | AC 3-5 | 12. | marker |
| 5. | AC 2-3 | 10. | AC 4-5 | | (from above 1.5, 1.2, 1.0, 0.9, 0.8, 0.7, |
| | | | | | 0.6, 0.5, 0.4, 0.3, 0.2, 0.1kbp) |

FIG. 6

```
                                                                                     Hirouchi 1'
rice genome    1 :  ------------ ------------ ------------ ------------ ------------ -V WTASAKMEYS AKTFRGKVSK
A.t          121 :  HLVTDFSPLR EIRRCKDEVV KRTSDSLAIH EVDAHNVVPM ------------ WAASSKLEYS ARTIRGKINK rice genome   31 :  VMDEYLVEFP --ELPAVVPW DREQPEGVDW DALI-------- ------------ -ARV------- ------------
A.t          181 :  LLPDYLIEFP KLEPPKKKWT GMMDKKLVDW DSLIDKVVRE GAEVPEIEWC VPGEDAGIEV rice genome   66 :  ------------ ------------ ------------ ------------ ------------ ---CRG------ ------------
A.t          241 :  LMGNKDGFLT KRLKNYSTDR NNPIKPKALS GLSPYLHFGQ VSAQRCALEA RKVRSTSPQA rice genome   83 :  VDAFLEELVV RRELADNFCY YQPQYDSLSG AMEWARKTLM DHAADKREHI Y---T------ ----QS------
A.t          301 :  VDIFLEELIV RRELSDNFCY YQPHYDSLKG AMEWARKSLM DHASDKREHI YSLEQLEKGL
                                                        Hirouchi 2' rice genome  141 :  NDYQLMNASQ LEWVHHGKMH GFM
A.t          361 :  TADPLMNASQ LEMLYQGKMH GFM
```

FIG. 7

```
                                                                    Hirouchi 1'
rice fragment    1 : ----------- ----------- ----------- ---------V WTASAKMEVS AKTERGKVSK
A.t fragment   121 : HLVTDFSPLR EIRRCKDEVV KRTSDSLAIH EVDAHNVVPM WAASKLEYS ARTIRGKINK
                                                                   GSP1  GSP2  GSP3   GSP4 rice fragment   22 : VMDEVIVEFP --ELPAVVPW DREQPEGVDM DALTARVCSE AENVPEIDMC EPGEEAAIEA
A.t fragment   181 : LLPDVLIEFP KLEPPKKKWT GMMDKKLVDW DSLIDKVVRE GAEVPEIEWC VPGEDAGIEV rice fragment   80 : ELGSKDGFLT KRIKSVETDR NDPTKPRALS GLSPYIHFGH ISAQRCALEA KKCRHLSPKS
A.t fragment   241 : LMGNKDGFLT KRLKNYSTDR NNEIKPKALS GLSPYIHFGQ VSAQRCALEA RKVRSTSPQA rice fragment  140 : VDAELEELVV RRELADNFCY YQPQYDSLSG AMEWMARKTLM DHAADKREHI YTREQLENAK
A.t fragment   301 : VDIFLEELIV RRELSDNFCY YQPHYDSIKG AMEWARKSLM DHASDKREHI YSLEQLEKGL Hirouchi 2'
rice fragment  200 : THDPLWNASO LEWVHHGKVH GFWRMYWAKK ILEWTSGPEE ALSTAIYLND KVEIDGRDPE
A.t fragment   361 : TNDPLWNASQ LEWLYQGKVH GFWRMYWAKK ILEWTKGPEE ALGISIYLNN KVEIDGRDPE rice fragment  260 : GYVGCWWSIC GLHDQGWKER PVFGKIRYMN YAGCKRKFDV DAYISYVKRL -AGQSKKRNA
A.t fragment   421 : GYVGCWWSIC GVHDQGWKER PVFGKIRYMN YAGCKRKENV DSYISYVKSL VSVTKKKRKA rice fragment  319 : EESPNPVVKL SKSQH*
A.t fragment   481 : EEQLTRDSVD PKITIV
```

FIG. 8

```
Gulfmont    1   : MPPT-SVSPP RTAPGPANPS PAHPSRVRVI HPGGGKPGGP VVYWMLRDQR LADNWALIHA
A.t         1   : MASTVSVQPG R--IRILKKG SWQPSDQTV- ---------GP VVYWMFRDQR LKDNWALIHA Gulfmont    60  : AGLAAASASP LAVAFALFPR PFFLSARRRQ LGFLLRGLRR LAADAAARHL PFFLFTGGPA
A.t         50  : VDLAMRTNAP VAWVENLF-- DQFLDAKARQ LGFMLKGLRQ LHHQIDSLQI PFFLLQGDAK Gulfmont    120 : E-IPALVRRL GASTHVADFS PLRPVREALD AVVGDLRREA PGVAVHQVDA HNVVPVVTAS
A.t         108 : ETIPNFLTEC GASHLVTDES PLREIRRCKD EVV---KRTS DSLAIHENDA HNVVPMWAAS Gulfmont    179 : AKMEYBAKTF RGKVSKVMDE VLVEEFP--EL PAVVPWDREQ PEGVDMDALI ARVCSEAENV
A.t         165 : SKLEYSARTI RGKINKLLPD YLHEFPKLEP PKKKWTGMMD KKLVDWDSLI DKVVREGAEV Gulfmont    237 : PEIDWCEPGE EAATEALLSS KDGFLTKRIK SVEFTDRNDPT KPRALSGLISP YLHFGHISAH
A.t         225 : PETEMCVPGE DAGHEVLMGN KDGFLTKRLR NYSTDRNNPI KPKALSGLSP YLHFGQVSAQ Gulfmont    297 : RCALEAKKCR HLSPKSVDAF LEELVRREL ADNFCYYQPQ YDSLSGAMEW ARKTMDHAA
A.t         285 : RCALEARKVR STSPQAVDIE LEELIVRREL SDNFCYYQPH YDSLKGAMEW ARKSLMDHAS
                                4bp Gulfmont    357 : DKREHIYTRE QLENAKTHDP LMNASQLEMV HHGKMHGFMR VVYWAKKILEM TSGPEEALST
A.t         345 : DKREHIYSLE QLEKGLTADP LWNASQLEML YQGKMHGFMR MYWAKKILEM TKGPEEALSI Gulfmont    417 : ATYINDKYEI DGRDPSGYVG CMMSICGLHD QGMKERPVFG KIRYMNYAGC KRKFDVD---
A.t         405 : SIYINNKYEI DGRDPSGYVG CWMSICGVHD QGMKERPVFG KIRYMNYAGC KRKFNVDSYI Gulfmont    474 : ---------ASFLM SRD------ --
A.t         465 : SYVKSLVSVT KKKRKAEEQL TRDSVDPKIT IV
```

GENE OF ENZYME REACTIVATING DNA DAMAGED BY ULTRAVIOLET LIGHT USING VISIBLE LIGHT

TECHNICAL FIELD

The present invention relates to a gene encoding a photoreactivating enzyme repairing DNA damaged by ultraviolet light, using visible light and a method for giving and enhancing the resistance to ultraviolet light, using the gene.

BACKGROUND OF THE INVENTION

One of the environmental concerns recently focused on is the destruction of the ozone layer. What influences are caused by the destruction on our life? The life of biological organisms on the earth is supported by sunlight, and simultaneously, hazardous ultraviolet light in sunlight constantly threatens the life. Ultraviolet light is a part of sunlight at a wavelength of 100 to 400 nm and is largely divided into three parts, namely UV-C at 100 to 290 nm, UV-B at 290 to 320 nm and UV-A at 320 to 400 nm. Specifically, ultraviolet light at a wavelength of 320 nm or less is absorbed in the ozone layer, while ultraviolet light at the other wavelengths, namely a part of UV-B and UV-A pour on the earth. Particularly, an ultraviolet light component at a wavelength close to the wavelength for DNA absorption at 260 nm, namely UV-B, causes a structural modification in the base regions of DNA. The modification includes two types of CPD and 6-4 adduct and both of them are dimers generated through a covalent crosslinking between two pyrimidine (Py) moieties adjacent to each other. When the modification generated in DNA by ultraviolet light is defined as 100%, CPD occupies 70 to 80% and the 6-4 adduct occupies 20 to 30%. These two structures inhibit DNA replication and transcription to cause cellular death and mutagenesis. It is believed that the onset of skin cancer caused by bathing in strong sunlight is triggered by these damages generated by ultraviolet light.

Biological organisms have various repair mechanisms for such damages. Therefore, biological organisms on the earth are not readily develop cancer even when they bath in sunlight. One of the mechanisms is photoreactivation. The repair system allows a photoreactivating enzyme to carry out the reverse reaction to that of Py+Py→CPD caused by ultraviolet light, using the energy of near ultraviolet light and blue light irradiated following ultraviolet light to return the CPD and 6-4 adduct generated by ultraviolet light to former state (1; FIG. 1). As the photoreactivating enzyme carrying out the repair, two types of enzyme exist; one specifically repairs CPD, while the other specifically repairs the 6-4 adduct (2,3). The presence of the CPD photoreactivating enzyme is confirmed widely among prokaryotic organisms and higher eukaryotic organisms. Once the ozone layer is destructed, the dose of ultraviolet light reaching the earth increases. Therefore, it is anticipated that more damages occur in DNA more than ever, leading to the limit of the repair, so that the biological organisms may be influenced by serious harms.

It is true with plants. Biological organisms with no direct need of sunlight can survive while avoiding sunlight, even if the dose of ultraviolet light increases. However, plants getting most of energy via photosynthesis cannot evade sunlight. Consequently, it is estimated that the influence of the destruction of the ozone layer on plants may be more serious than on biological organisms with no direct need of sunlight.

An experiment is reported recently, where *Arabidopsis thaliana* and *Nicotiana* were grown in environment at a higher ultraviolet light dose based on a possible decrease of the ozone layer in future as estimated from the current basal value of the dose of ultraviolet light (4). In other words, actual influences on plants were observed in a potential status assumed on the basis of the destruction of the ozone layer. The results are as follows. First, the dose elevation increases the cellular CPD and 6-4 adducts from the current levels, so that their growth is suppressed and their genes are increasingly recombined, leading to the elevation of the instability of the genomes, which involves the increase of the instability in the course of generations. In other words, the elevated ultraviolet light not only influences the generation itself but also gives such influences over some future generations. When the dose irradiated is retained, further, more mutations accumulate in a later generation, so that the generation turns more sensitive to ultraviolet light than preceding generations. This is due to the fact that *Arabidopsis thaliana* or *Nicotiana* is more influenced by ultraviolet light because *Arabidopsis thaliana* or *Nicotiana* is exposed to the external atmosphere during the term from the dehiscence of the anther as a reproductive organism to the stage of pollination with the pollen of *Arabidopsis thaliana* or *Nicotiana*. This is the case with most of plants on the earth. It may be considered that those described about *Arabidopsis thaliana* and *Nicotiana* can be induced by the destruction of the ozone layer and the subsequent increase of the dose of ultraviolet light. In other words, this suggests a possibility of the emergence of a severe change in the ecosystem some years after the destruction of the ozone layer.

As described above, it can be said that photoreactivation capable of reducing the influences of ultraviolet light using the energy of visible light supplied by sun in the same manner as for ultraviolet light is a considerably effective ultraviolet protective system for plants hardly capable of avoiding the influences of ultraviolet light in sunlight. A report showing the presence of photoreactivation in higher plants is issued, for supporting those described above.

A report suggests the presence of CPD photoreactivation activity in a higher plant "*Oryza*" particularly familiar to the Japanese. At the experiment, an appropriate dose of ultraviolet light irradiates the leaf (third leaf) of *Oryza*, which is subsequently irradiated with visible light (blue light). Then, the amount of CPD in the cells decreases (repairing) in proportion to the duration of visible light irradiation. Depending on the level of visible light irradiated on an individual after germination, additionally, the CPD repair efficiency of the individual was elevated (5). In other words, a larger amount of CPD can be repaired by the same dose of visible light. The CPD photoreactivation activity never similarly occurs in all of *Oryza* species. An *Oryza* species (Norin No. 1) with poor ultraviolet resistance is repaired at a slow rate, compared with an *Oryza* species (Sasanishiki) resistant to ultraviolet light (6). This may possibly be ascribed to the occurrence of some mutation in the photoreactivating enzyme itself in the species with poor ultraviolet resistance or the system regulating the expression. However, the cause has not yet been elucidated.

References and information of the related art in relation with the invention of this application are as follows.
(1) Aziz Sancar. (1994) "Structure and Function of DNA photolyase" Biochemistry 33:2–9.
(2) Takeshi Todo, Hiroshi Takemori, Haruko Ryo, Makoto Ihara, Tsukasa Matsunaga, Osamu Nikaido, Kenji Sato, Taisei Nomura (1993) "A new photoreactivation enzyme that specifically repairs ultraviolet light-induced (6-4) photoproduct" Nature 361:371–374.
(3) Aziz Sancar (1996) "No "End of History" for Photolyases " Science 272:48–49
(4) Gerhard Ries,Werner Heller,Holger Puchta,Heninrich Sandermann,Harald K.Seidlitz, Barbaara Hohn (2000) "Elevated UV-B radiation reduces genome stability in plants" Nature 406
(5) Hye-Sook Kang, Jun Hidema and Tadashi Kumagai (1998) "Effects of light environment during culture on UV-induced cyclobutyl pyrimidine dimers and their photorepair in rice (*Oryza sativa* L.)" Photochemistry and Photobiology 68: 71–77
(6) Jun Hidema, Tadashi Kumagai, John C. Sutherland, Betsy M Sutherland (1997) "Ultraviolet B-sensitive rice cultivar deficient in cyclobutyl pyrimidine dimer repair". Plant Physiology 113: 39–44
(7) Satoshi Nakajima, Munetaka Sugiyama, Shigenori Iwai, Kenichi Hitomi,Eriko Otoshi,Sang-Tae Kim,Cai-Zhong Jiang,Takishi Todo,Anne B Britt, Kazuo Yamamoto (1998) "Cloning and characterization of a gene (UVR3) required for photorepair of 6-4 photoproducts in *Arabidopsis thaliana*" Nucleic Acid Research 26:638–644
(8) Jason L.Petersen,Darin W.Lang, Gary D.Small (1999) "Cloning and characterization of a class II DNA photolyase from Chlamydomonas" Plant Molecular Biology 40 :110633–1071
(9) Yao-Guang Liu, Kiyotaka Nagaki, Masao Fujita, Kanako Kawaura, Masahiko Uozumi, Yasunari Ogihara. (2000) "Development of an efficient maintenance and screening system for large-insert genomic DNA libraries of hexaploid wheat in a transformation-competent artificial chromosome (TAC) vector." The Plant Journal 23:687–95.
(10) Kazuo Maruyama, Sumio Sugano (1994) "oligo-capping:a simple method to replace the cap structure of eukaryotic mRNAs with oligoribonucleotides" Gene 138: 171–174
(11) Michael Herrler (2000) "Use of SMART-generated cDNA for Differential Gene Expression Studies " Jounal of Molecular Medicine 78:B23.

DISCLOSURE OF THE INVENTION

It is an object of the invention to obtain the information about the plant photoreactivation mechanism not so much elucidated yet, by isolating a photoreactivating enzyme from an *Oryza* species (Sasanishiki) resistant to ultraviolet light, where the presence of a photoreactivating enzyme is suggested as described above and to give a solution of environmental problems brought about by the destruction of the ozone layer and a solution of a serious problem in the 21 century, namely the food problem by preparing plants resistant to ultraviolet light using a cloned gene.

Accordingly, the invention relates to the following individual aspects.

1. A gene encoding a photoreactivating enzyme derived from *Oryza*.
2. The gene described in the aspect 1, where the gene encodes a pyrimidine dimer photoreactivating enzyme.
3. The gene described in the aspect 1 or 2, where the gene is derived from the species resistant to ultraviolet light.
4. The gene described in the aspect 1, 2 or 3, where the *Oryza* species is Sasanishiki.
5. The gene described in the aspect 1, where the *Oryza* species is Gulfmont.
6. A gene including a nucleotide sequence encoding the following protein (a) or (b):
(a) a protein comprising an amino acid sequence at the 174th position to 506th position from the N terminus of SEQ ID No.1;
(b) a protein comprising an amino acid sequence derived from the amino acid sequence (a) by deletion, substitution or addition of one to several amino acids, and having the activity of a photoreactivating enzyme.
7. A gene including the following DNA (a) or (b):
(a) DNA including base pairs at the 520th position to 1521st position in the nucleotide sequence of SEQ ID No.2;
(b) DNA hybridizing with the DNA comprising the nucleotide sequence (a) under stringent conditions and encoding a protein with the activity of a photoreactivating enzyme.
8. A gene encoding the following protein (a) or (b):
(a) a protein comprising the amino acid sequence of SEQ ID No.1;
(b) a protein comprising an amino acid sequence derived from the amino acid sequence (a) by deletion, substitution or addition of one to several amino acids, and having the activity of a photoreactivating enzyme.
9. A gene including the following DNA (a) or (b):
(a) DNA comprising the nucleotide sequence of SEQ ID No.2;
(b) DNA hybridizing with the DNA including the nucleotide sequence (a) under stringent conditions and encoding a protein with the activity of a photoreactivating enzyme.
10. A method for preparing a gene described in any one of the aspects 1 through 9, including a step of screening an *Oryza* gene library by repeating dilution PCR.
11. The method described in the aspect 10, where the *Oryza* gene library is a cDNA library.
12. The method described in the aspect 11, where *Oryza* is Sasanishiki or Gulfmont.
13. A recombinant expression vehicle containing a gene described in any one of the aspects 1 through 9.
14. The recombinant expression vehicle described in the aspect 13, where the recombinant expression vehicle is lamda phage.
15. The recombinant expression vehicle described in the aspect 13, where the recombinant expression vehicle is a plasmid vector.
16. A transformant prepared by transformation with an expression vehicle described in the aspect 13, 14 or 15.
17. The transformant described in the aspect 16, where the transformant is a plant.
18. The transformant described in the aspect 17, where the plant is *Oryza*.
19. The transformant described in the aspect 16, where the transformant is *Escherichia coli*.
20. A method for giving the resistance to ultraviolet light to a host or enhancing the resistance of a host against ultraviolet light, including a step of transforming the host with a gene described in any one of the aspects 1 through 9.
21. The method described in the aspect 20, where the host is a plant.
22. The method described in the aspect 21, where the plant is *Oryza*.
23. The method described in the aspect 22, where *Oryza* is of a species sensitive to ultraviolet light.
24. The method described in the aspect 23, where the species of *Oryza* sensitive to ultraviolet light is Norin No. 1.
25. A method for screening the expression level of the gene of a photoreactivating enzyme in *Oryza*, using a gene described in any one of the aspects 1 through 9 or a DNA fragment thereof.

26. A method for assaying the transcription level of the gene of a photoreactivating enzyme to mRNA in *Oryza* by a Northern hybridization method using a gene described in any one of the aspects 1 through 9 or a DNA fragment thereof.
27. The method described in the aspect 25 or 26, where *Oryza* is of a species resistant to ultraviolet light and/or sensitive to ultraviolet light.
28. A polypeptide or protein encoded by a gene described in any one of the aspects 1 through 9.
29. The polypeptide or protein described in the aspect 28, where the polypeptide or protein has the activity of a photoreactivating enzyme.
30. A method for preparing a gene encoding a photoreactivating enzyme derived from a plant, including a step of preparing a first primer based on a highly homologous region in amino acid sequence between at least two types of existing photoreactivating enzymes, a step of cloning a first DNA fragment using the genome of the plant as template by PCR using the first primer, a step of preparing a second primer based on a highly homologous region in amino acid sequence between the first DNA fragment and the photoreactivating enzyme of *Arabidopsis thaliana*, a step of cloning a second DNA fragment using the plant gene library as template by PCR using the second primer, and a step of cloning the objective gene by a nucleic acid hybridization method using the second DNA fragment as a probe.
31. The method described in the aspect 30, where the existing photoreactivating enzymes are the photoreactivating enzymes of *Arabidopsis thaliana* and Chlorophyceae.
32. The method described in the aspect 30 or 31, where the plant gene library is a cDNA library.
33. The method described in the aspect 30, 31 or 32, where the nucleic acid hybridization method is a plaque hybridization method.
34. The method described in any one of the aspects 30 through 33, where the plant is *Oryza*.
35. The method described in the aspect 30, where the gene is a gene described in any one of the aspects 1 through 9.

BRIEF DESCRIPTION OF THE DRAWINGS

FIG. 2 shows the comparison in amino acid sequence of photoreactivating enzyme between *Arabidopsis thaliana* (SEQ ID NO: 3) and Chlorophyceae (SEQ ID NO: 4). A.t expresses *Arabidopsis thaliana* and C.r expresses Chlorophyceae, while AC1 to AC5 express primer positions.

FIG. 6 shows the comparison between the amino acid sequence speculated from the *Oryza* genome AC1.1 kbp (SEQ ID NO: 5) and the amino acid sequence of the CPD photoreactivating enzyme in *Arabidopsis thaliana* (SEQ ID NO: 6). Herein, portions with double underlines show the positions of perfect match primers.

FIG. 7 shows the comparison in amino acid sequence between a CPD photoreactivating enzyme fragment in the *Oryza l genome (SEQ ID NO: 7)* and the CPD photoreactivating enzyme in Arabidopsis thaliana (SEQ ID NO: 8). Herein, portions with double underlines show the positions of perfect match primers.

FIG. 8 shows the comparison in amino acid sequence between a CPD photoreactivating enzyme fragment in the Oryza (Gulfmont) (SEQ ID) NO: 9) and the CPD photoreactivating enzyme in *Arabidopsis thaliana* (SEQ ID NO: 10).

BEST MODE FOR CARRYING OUT THE INVENTION

Figure 1:
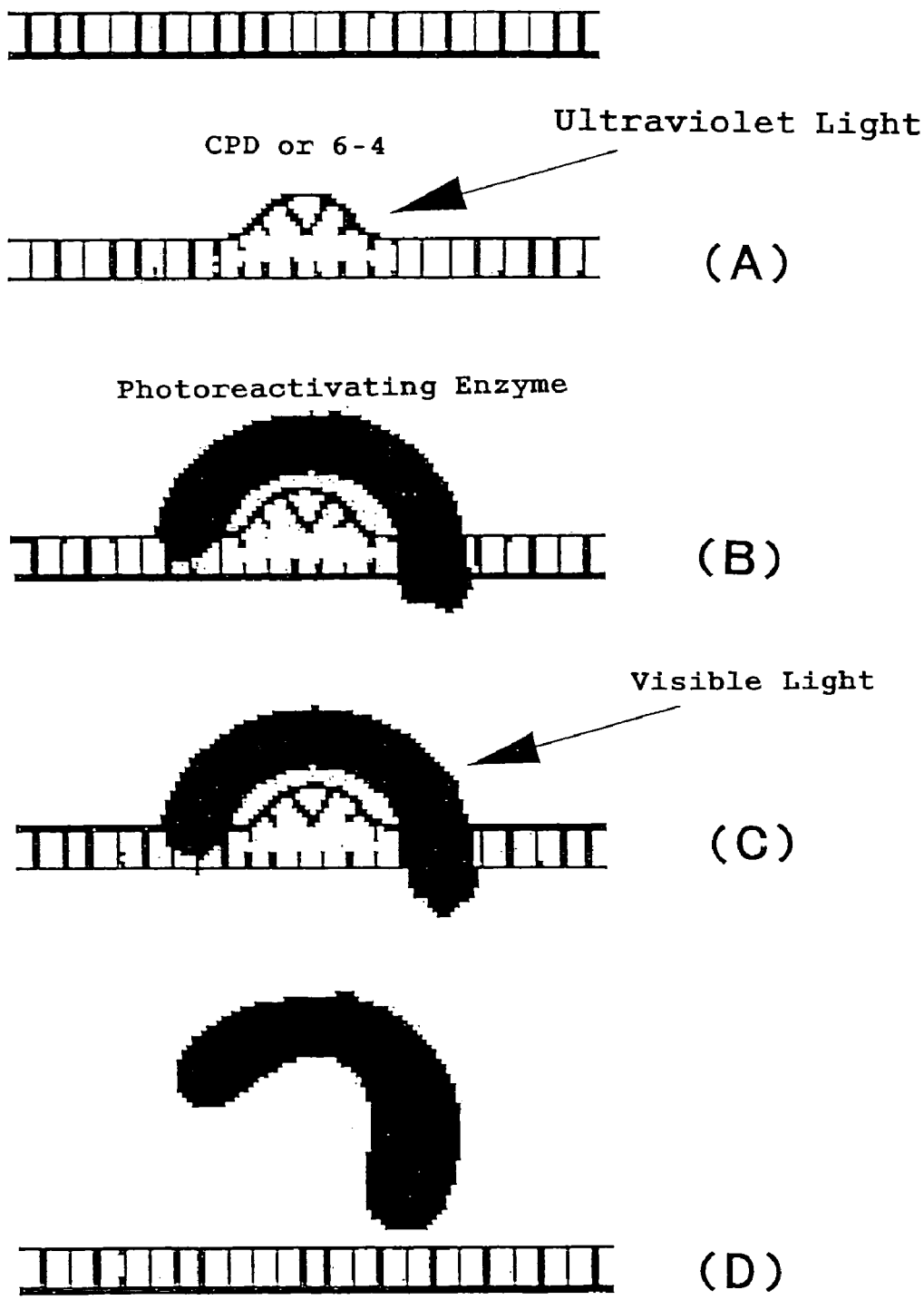
FIG. 1 shows the photoreactivation mechanism. Ultraviolet light generates CPD or 6-4 adduct on the DNA strand (A). The CPD photoreactivating enzyme and the 6-4 adduct photoreactivating enzyme is bound specifically to the CPD and the 6-4 adduct, respectively (B), to bring back the individual damages to the original states under irradiation of visible light (near ultraviolet light, blue light) (C). Consequently, the photoreactivating enzymes are dissociated from the DNA strand (D).

As shown in the following Examples, the individual genes encoding the photoreactivating enzyme derived from *Oryza* in accordance with the invention was prepared, using for example the cDNA libraries derived from "Sasanishiki" as an *Oryza* species with resistance to ultraviolet light as disclosed in the specification and "Gulfmont", by PCR using appropriate primers prepared in accordance with the invention, particularly the primers prepared on the basis of the amino acid sequence highly conserved between the pyrimidine dimer (CPD) photoreactivating enzymes from *Arabidopsis thaliana* and Chlorophyceae. By repetition of the dilution PCR, in particular, gene libraries such as the cDNA libraries of *Oryza* were screened to recover the gene of the invention efficiently.

The invention relates to a gene containing a nucleotide sequence encoding the protein comprising the amino acid sequence from the 174th position to 506th position from the N terminus of SEQ ID No. 1, particularly a gene with an additional appropriate nucleotide sequence on the 5' side. The sequence is preferably derived from *Oryza*, for example "Sasanishiki". One example thereof includes a gene encoding the protein of the amino acid sequence represented by SEQ ID No.1.

Based on the sequence information disclosed in the specification, a person skilled in the art can prepare such gene by chemical synthesis and the like using well known techniques in the art. Further, a person skilled in the art can readily carry out the deletion, substitution or addition of one to several amino acids in a specified amino acid sequence in SEQ ID No.1 by using well known techniques in the art, so that the photoreactivating enzyme activity may be substantially conserved.

The specific example of the above-described gene includes a gene containing DNA including base pairs at the 520th position to 1521st position in the nucleotide sequence of SEQ ID No.2, particularly a gene containing DNA of the nucleotide sequence of SEQ ID No.2.

In accordance with the invention, a specific gene or DNA can be hybridized in a buffer solution well known to a person skilled in the art under stringent conditions of various conditions such as appropriate temperature and salt concentration. The DNA being hybridizable to the gene or DNA of the invention under such stringent conditions and still having an activity substantially equivalent to the photoreactivating enzyme includes for example DNA with homology of 90% or more, preferably 95% or more, more preferably 98% or more and furthermore preferably more than 99.5% to each of the corresponding genes.

Further, in another embodiment, further, the invention relates to a recombinant expression vehicle carrying at least one gene of the gene in accordance with the invention. The recombinant expression vehicle includes appropriate ones known to a person skilled in the art, such as various vectors. Particularly, various plasmid vectors such as Ti plasmid contained in bacteria of the genus *Agrobacterium* and phage vectors such as lamda phage are preferable.

The recombinant expression vehicle may include various sequences known to a person skilled in the art for gene recombinant manipulation, for example various promoters as binding domains for various σ subunits as transcription factors in prokaryotic cells such as *Escherichia coli*, and various transcription regulatory elements such as enhancer, restriction enzyme sites, as well as genes of selection markers (marker enzymes, etc.) such as kanamycin resistant marker and the recombinant expression vehicle can be readily prepared by methods known to a person skilled in the art.

The invention further relates to a host, transformed by the above expression vehicle, particularly a plant such as *Oryza*.

The transformation of a host with the gene of the invention can give or enhance the resistance to ultraviolet light in the host. The host is preferably plants for example *Oryza*, particularly an *Oryza* species sensitive to ultraviolet light, such as "Norin No. 1".

Using the gene of the invention or a DNA fragment thereof as, for example, a probe, the expression level of a photoreactivating enzyme gene in plants such as *Oryza* can be screened. This can be done by assaying the transcription level of the photoreactivating enzyme gene to mRNA in *Oryza* by the Northern hybridization method using the gene of the invention or a DNA fragment thereof as a probe.

Further, the invention relates to a polypeptide or protein with a photoreactivating enzyme activity, as encoded by the gene of the invention. The polypeptide or protein can be prepared by culturing the transformant and using the resulting culture supernatant or the resulting bacterial cell. As to the culture conditions and the separation and purification from the culture supernatant, a person skilled in the art can appropriately select such conditions and the like with reference to the Examples in this specification.

The invention further relates to a method for preparing a gene encoding a photoreactivating enzyme derived from a plant, including a step of preparing a first primer based on a highly homologous region in amino acid sequence between at least two types of existing photoreactivating enzymes, a step of cloning a first DNA fragment using the genome of the plant as template by PCR using the first primer, a step of preparing a second primer based on a highly homologous region in amino acid sequence between the first DNA fragment and the photoreactivating enzyme of *Arabidopsis thaliana*, a step of cloning a second DNA fragment using the plant gene library as template by PCR using the second primer, and a step of cloning the objective gene by a nucleic acid hybridization method using the second DNA fragment as a probe. The existing photoreactivating enzymes are the photoreactivating enzymes of *Arabidopsis thaliana* and *Chlorophyceae*. There is no limitation as to the source used for recovering a sample used for preparing the plant gene library, however, cDNA library is preferable. The nucleic acid hybridization method includes any method known to a person skilled in the art, for example plaque hybridization method and Southern hybridization method. Further, the plant includes for example *Oryza*, wheat, and barley. By such method, the gene of the invention can be prepared.

The contents described in the Japanese Patent Application 2001-320138 are all included in this specification.

EXAMPLES

The invention is now specifically described in the following Examples. However, the invention is not limited to these Examples.

Materials and Methods

1. *Escherichia coli* and Plasmids

The *Escherichia coli* used was XL1-Blue (Δ(lac), endA1, gyrA96, hsdR17 (rk−,mk+), recA1, relA1, supE44, thi-1, [F',lac1q, lacΔM15, proAB, Tn 10 (tet$^r$)]) N K J 3 0 0 2 (Δ(lac-proAB), endA1, gyrA96, hsdR17 (rk−,mk+), relA1, supE44, thi-1, phr20::Kan uvrA::Kan ΔrecA, [F',lac1q, lacZ Δ M15, proAB]). pGEM-T and pGEM-T easy vector (Promega) were used for the cloning of PCR products. So as to examine the photoreactivation ability of the cloned CPD photoreactivating enzyme gene from Sasanishiki, the gene was integrated in the pTZ18R vector (PHARMACIA) and then introduced in *Escherichia coli*.

2. Preparation of cDNA Library of *Oryza* Sasanishiki

The *Oryza* species was grown in the environment under the irradiation of visible light since the germination of *Oryza* seed until the third to sixth leaves opened. Then, mRNA was extracted from the individual leaves. Using mRNA as template, cDNA was synthetically prepared. An adapter was ligated to both ends of the cDNA and was then packaged in Lamda ZAP II (STRATAGENE), to prepare the library.

3. Preparation and Sequencing of Mix Primers

Based on the amino acid sequences at five positions (FIG. 2; AC1 to AC5) where the amino acid sequences were highly conserved between the CPD photoreactivating enzymes from *Arabidopsis thaliana* (7) and *Chlorophyceae* (8), mix primers were prepared. Using about 1 μg of the *Oryza* genome as template, PCR was conducted ([$Mg^{2+}$]=2.0 mM; 93° C. for 1 min; 40 cycles of <<93° C. for 1 min, 53° C. for 1 min and 72° C. for 1.5 min>>; 72° C. for 10 min.: Gene Amp 480/9600 System by Perkin Elmer). The PCR product was cloned in pGEM-T or the pGEM-T easy vector (Promega), and its nucleotide sequence was determined via fluorescent labeling using ABI PRISM BigDye Terminator Cycle Sequencing Ready Reaction Kits or the DYEnamic ET terminator Cycle Sequencing pre-mix kit by 310 Genetic Analyzer or 373 Genetic Analyzer (Perkin Elmer).

4. Screening of Lamda ZAP II/Rice cDNA Library by Plaque Hybridization

About 15,000 to 20,000 plaques of Lamda phage (Lamda ZAP II/rice cDNA library) were grown on a culture medium and then covered with sterilized Gene Screen plus (NEN Life Science Products) for transfer. The transferred Gene Screen plus was immersed in a denature solution (0.5N NaOH, 1.5M NaCl) for 5 minutes, and continuously immersed in a nautring solution (0.5M Tris-HCl, 1.5M NaCl) for 5 minutes and then in 2×SSC solution for 5 minutes, and spontaneously dried for 30 to 60 minutes, followed by baking in a dry heat sterilizer at 80° C. for 2 hours. This was treated with 3×SSC (65° C.) for 30 minutes and a pre-hybridization solution (5×SSC, 1% SDS, 1×Denhart: 65° C.) for 2 hours, and mixed about 25 ng of a $^{32}$P-labeled probe in a hybridization solution (0.75 M NaCl, 20 mM Tris-HCl, pH 8.0, 2.5 mM EDTA, pH 8.0, 1% SDS, 1×Denhart, 10 µg/ml sermon sperm DNA). The resulting mixture was kept overnight at 65° C. (hybridization). The Gene Screen plus after overnight hybridization was taken out and rinsed in a solution of 2×SSC and 0.1% SDS for 5 minutes and twice in a solution of 0.2×SSC and 0.1% SDS (65° C.) for 30 minutes. Then, the resulting product was covered with FUJI MEDICAL X-ray FILM (FUJI FILM) for exposure and development. A plaque with developed signals was recovered from the culture medium. A plaque was formed on a fresh culture medium and for confirmation, the plaque hybridization was again carried out by the same procedures. The plaque was transferred on pBlueScript SK(-) for the determination of the nucleotide sequence of the insert.

5. Genome Walking

About 5 µg of the genome extracted from the *Oryza* was treated with four types of restriction enzymes (Dra I, EcoR V, Stu I, Pvu II), for adapter ligation (see Universal Genome Walker Kit Manual manufactured by CLONTECH). Using the resulting ligate as template, PCR was conducted using the adapter primer and the primers prepared on the basis of the cDNA sequence of *Oryza* as already determined ([$Mg^{2+}$]= 2.0 mM; 93° C. for 1 min; 40 cycles of <<93° C. for 1 min, 50–55° C. for 1 min and 72° C. for 1.5 min>>; 72° C. for 10 min.: Gene Amp 480/9600 System by Perkin Elmer). The resulting PCR product was applied to electrophoresis and then transferred on Gene Screen plus for Southern hybridization, to screen the intended bands. Again, the PCR product was developed by electrophoresis on low melting agar (LMA), to extract a band with signals, which was then cloned into pGEM-T or the pGEM-T easy vector (Promega) for sequencing.

6. Screening the *Oryza* Gulfmont cDNA/pSPORT-T Library or the Sasanishiki cDNA/pBS SK(-)/Lamda Zap II Library The screening of SUPERSCRIPT RICE (cv. Gulfmont) LEAF cDNA library and the manufactured by GIBCO BRL Sasanishiki cDNA/pBS SK(-) library prepared by transferring the Lamda ZAP II/rice cDNA library in pBS SK(-) plasmid was conducted by the dilution PCR ([$Mg^{2+}$]=1.0 mM; 93° C. for 1 min; 40 cycles of <<93° C. for 1 min, 60° C. for 1 min and 72° C. for 1.5 min>>; 72° C. for 10 min.: Gene Amp 480/9600 System by Perkin Elmer). So as to determine the ratio of the target plasmid (the cDNA of the CPD photoreactivating enzyme) at the state of stock solution ($5\times10^9$ *Escherichia coli* cells/ml), the stock solution was diluted by every $10^{-1}$ order to $10^{-2}$, $10^{-3}$, $10^{-4}$, $10^{-5}$, $10^{-6}$, and $10^{-7}$ in each volume of 5 ml. Then, the diluted solutions were cultured up to the stationary phase for amplification, from which the plasmid was extracted for PCR. 5 ml of the $10^{-6}$-fold dilution solution did not contain the target, while 5 ml of the $10^{-5}$-fold dilution solution contained the targets 1 to 9. A liquid culture of 5 ml of a solution at the most diluted concentration of $10^{-5}$ involving signal generation was again prepared and divided into 10 portions (#1 to 10), which were individually cultured up to the stationary phase for amplification. Then, the plasmid was extracted for PCR (FIG. 3). #1 and #3 contain the target at a concentration 10-fold higher than the concentration in the stock solution. The liquid culture involving signal generation was treated by the same procedures as for the stock solution in a repeated manner, to target just one colony.

Results and Discussion (1) Preparation of Mix Primers

Figure 4:
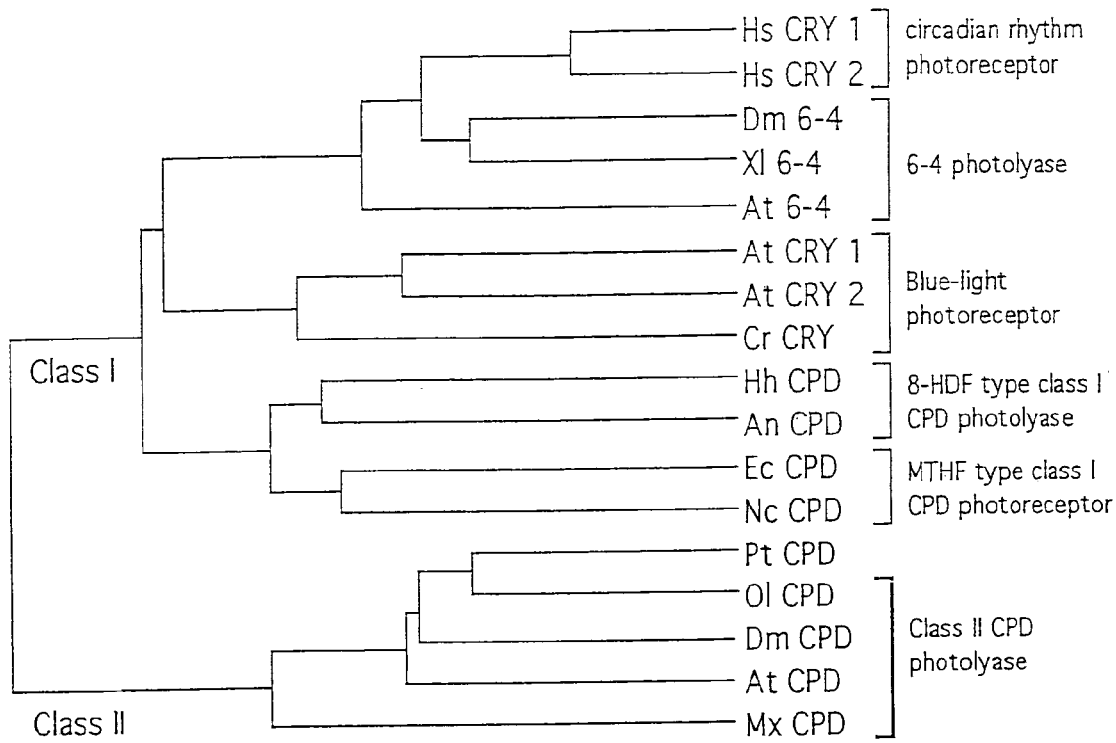
FIG. 4 shows an evolution tree for photoreactivating enzymes, blue color receptors and the circadian rhythm receptor family.

Currently, CPD photoreactivating enzymes have been isolated from various biological organisms. They are homologous to the blue receptors in plants and the genes responsible for human circadian rhythm, and form one family (FIG. 4). Based on the difference in amino acid sequence, they are broadly divided into two groups. With some exception, the two groups are Class I to which microorganisms such as *Escherichia coli* belongs and Class II to which higher eukaryotic organisms belong. Among plants, *Arabidopsis thaliana* and *Chlorophyceae* with isolated CPD photoreactivating enzymes belong to Class II. Because *Oryza* as a current experimental subject is a higher eukaryotic organism, it is assumed that the amino acid sequence of the photoreactivating enzyme thereof may belong to those of Class II, like *Arabidopsis thaliana* and *Chlorophyceae*. On the comparison in amino acid sequence between *Arabidopsis thaliana* and *Chlorophyceae*, primers were synthetically prepared on the basis of the five regions with higher homology (FIG. 2). As several types of codons correspond to one amino acid determination, the primers are mix primers containing all the nucleotide sequences corresponding to the amino acid sequences at the individual regions. If it is confirmed by PCR for all possible combinations of the five primers that the primary structure of the presently used photoreactivating enzyme of *Oryza* contains the same amino acid sequence as the original amino acid sequence working for the primer preparation, it suggests that the genome DNA includes the presence of a nucleotide sequence corresponding thereto. In that case, theoretically, the nucleotide sequence in the sequence can be amplified and determined by PCR.

(2) PCR Using *Oryza* Genome DNA as Template

Figure 5:
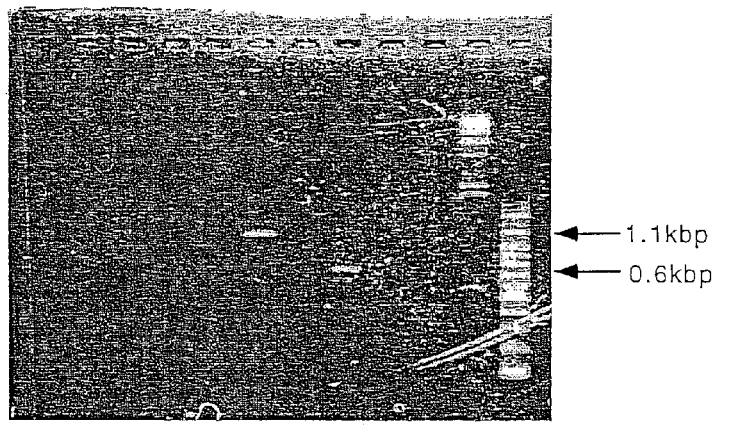
FIG. 5 shows the amplification of the coding region of the CPD photoreactivating enzyme in the *Oryza* genome with mix primers.
Figure 9:
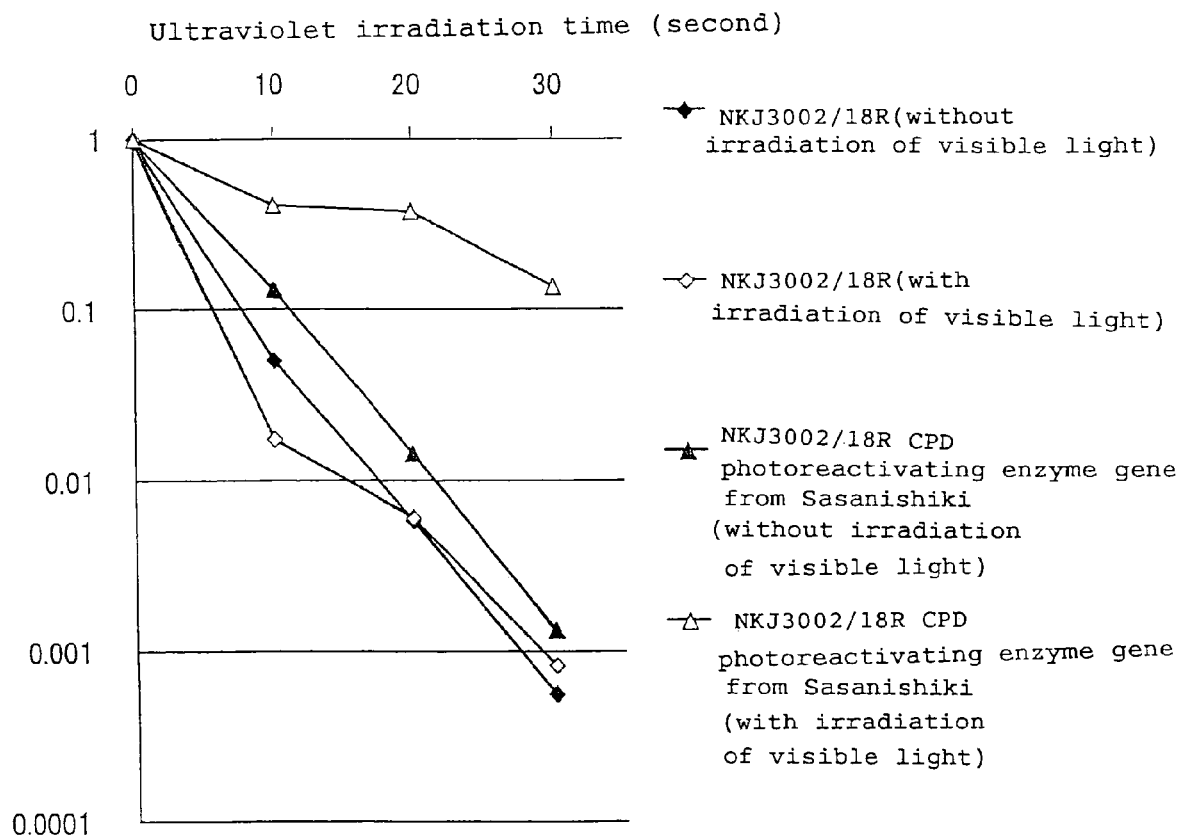
FIG. 9 shows the results of a complementarity test verifying that the photoreactivating enzyme of the invention has photoreactivation ability, using an *Escherichia coli* strain deficient in repairing.

FIG. 5 shows actual PCR with the primers AC1 to AC5 described above, using the *Oryza* genome DNA as template. AC 1–2 and the like show primer combinations; the AC 1–2 shows the coding region of the CPD photoreactivating enzyme of the *Oryza* genome in the primers AC1 and AC2. Consequently, a combination of AC2 and AC4 gave a DNA fragment of about 1.1 kbp, while a combination of AC3 and AC4 gave a DNA fragment of about 600 bp. As shown in the figure, the 600-bp fragment is not amplified at a level as high as the level for the 1.1-kbp fragment. AC 2–4 includes 245 amino acids (735 bp) in *Arabidopsis thaliana* or 244 amino acids (732 bp) in *Chlorophyceae*. AC 3–4 includes 127 amino acids (381 bp) in *Arabidopsis thaliana* and also 127 amino acids (381 bp) in *Chlorophyceae*. It is estimated that because an intron may exist in the genome DNA's, the sequence will be longer than this. Thus, the fragments of 1.1 kbp and 600 bp might be the intended fragments. Even under modified temperature condition and $Mg^{2+}$ concentration, totally no PCR product was obtained with other primers. The PCR product was cloned into the pGEM-T vector (CLONTECH), to determine the sequences of the 1.1-kbp fragment of AC 2–4 and the 600-bp fragment of AC 3–4 to speculate their amino acid sequences. Its comparison with the amino acid sequence of the CPD photoreactivating enzyme of *Arabidopsis thaliana* shows high homology to the amino acid sequence from the 1.1-kbp DNA sequence (FIG. 6). Because the 600-bp fragment was not so much amplified by PCR as described above, it is considered because the primer might have annealed to a sequence similar to the original amino acid sequence and then amplified, the fragment might have been a background.

(3) Screening of *Oryza* cDNA Library

So as to obtain a cDNA fragment without intron, a primer was prepared from a region with high homology to the CPD photoreactivating enzyme of *Arabidopsis thaliana* (the underlined part in FIG. 6) in the 1.1-kbp sequence. Using the primer, and using the *Oryza* cDNA as a template, PCR was conducted (93° C. for 1 min; 40 cycles of <<93° C. for 1 min, 55° C. for 1 min and 72° C. for 1.5 min>>; 72 C. for 10 min.: Gene Amp System by Perkin Elmer)), to obtain a 600-bp fragment. In the same manner as in the case of the genome DNA, the sequence was determined to speculate the amino acids, which was compared with that of the CPD reactivation enzyme of *Arabidopsis thaliana*. It was confirmed that these amino acids were highly homologous at the same positions as that of the 1.1-kbp fragment of the genome DNA. Further, using the cDNA fragment as a probe, the Lamda ZAP II/Rice cDNA library as the starting material for the 600-bp template was used for plaque formation, for screening by Southern hybridization several times. About 200,000 plaques were screened, so that two candidates were obtained. The nucleotide sequence of DNA packaged in each of the two plaques was determined. It was shown that both the plaques had the same sequence, which was a 1.1-kbp cDNA fragment including the 600-bp probe partially deficient in a sequence at the 5' side up to the 3' terminus (C terminus) (FIG. 7). The deficiency at the 5' side may be ascribed to the decomposition of the probe from the 5' side with RNase attached on the device and the like, before cDNA formation by the reverse-transcription of mRNA as the template for the cDNA. Because the decomposition is not uniform, the cDNA library contains fragments of various lengths deficient in a sequence at the 5' side in addition to the full-length fragment. This is the case with the 1.1-kbp fragment obtained by the plaque hybridization. A possibility remains that a fragment of a length closer to the full length may be obtained by carrying out the same experiment again. However, such fragment could not be obtained by the several experiments using the library.

(4) Genome Walking Method of *Oryza* Genome DNA

Because the approach from the cDNA library was difficult as described above, the genome walking method was carried out for hardly readily decomposed genome DNA unlike cDNA. As described in the "Materials and Methods", *Oryza* genome DNA was treated by four restriction enzyme types (Dra I, EcoR V, Stu I, Pvu II), and an adapter was ligated to the resulting digestion products (Genome Walker Library: CLONTECH). Using the resulting products as a template, PCR with a primer for the ligated adapter and the prepared perfect match primers was conducted. Consequently, plural DNA fragments were obtained by PCR using the library treated with Pvu II as template and GSP4 and the primer for the adapter. Then, by Southern hybridization, the intended fragment was narrowed down around 500 bp among the resulting plural PCR products, cloned and determine the sequences. Consequently, a region of only 100 bp at the 5' side was confirmed, which was unknown (no homology to other CPD photoreactivating enzymes could be observed even after the conversion to amino acid sequence). Libraries except for the Pvu II library could not be well screened by Southern hybridization. Thus, not any more effect could be obtained.

(5) Screening of Different *Oryza* cDNA Library

Figure 3:
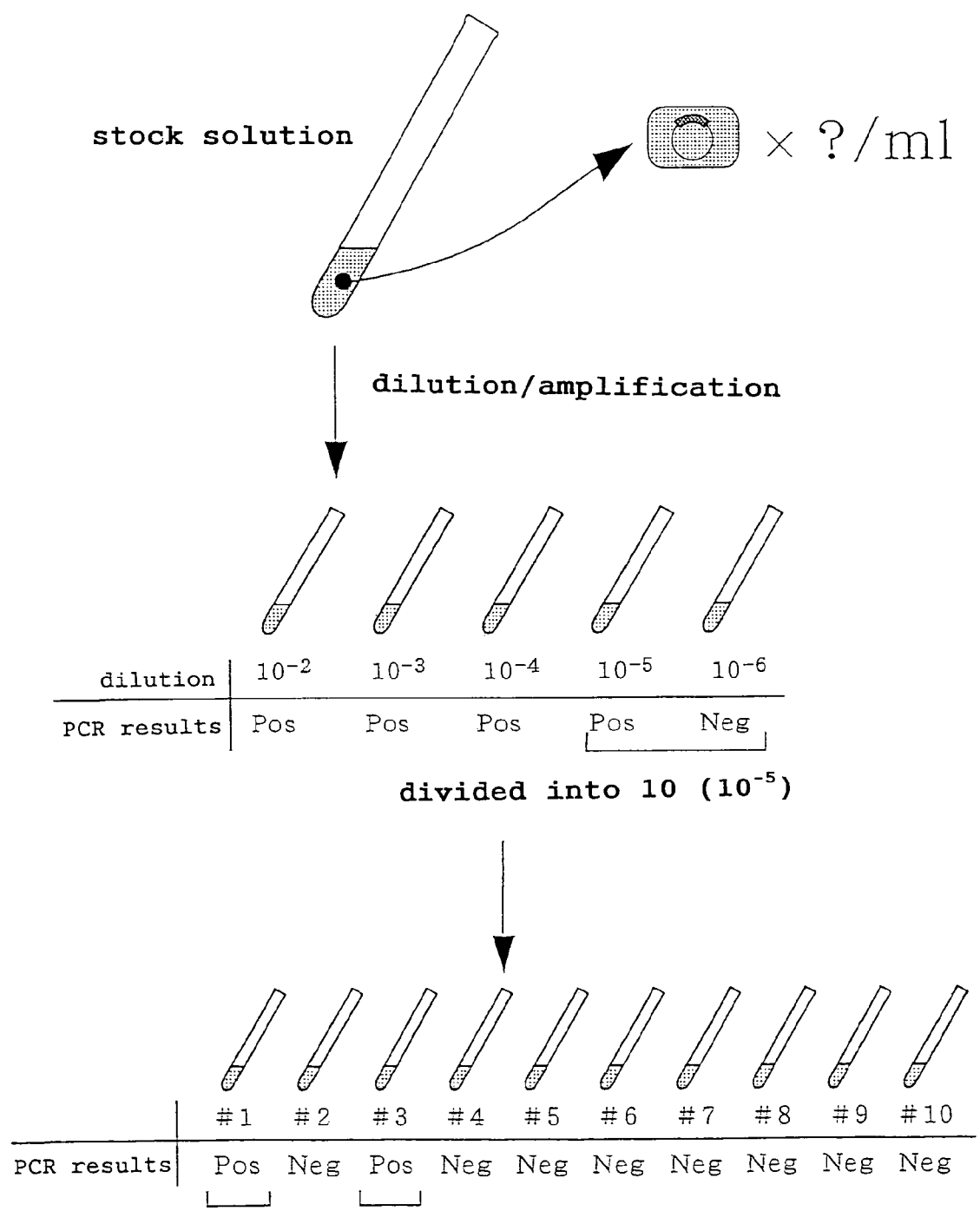
FIG. 3 shows a schematic view of screening the *Oryza* Gulfmont cDNA/pSPORT-T library and the Sasanishiki cDNA/pBSSK(−) library.

As described above, only fragments with the deficiency at the 5' side were obtained from the *Oryza* (Sasanishiki) Lamda ZAP II/cDNA library. Accordingly, the present inventors screened the pSPORT-T/rice (Gulfmont) cDNA library prepared via another route. The Gulfmont species is a species produced in USA and its photoreactivation activity has not yet been examined. Screening was conducted using as a marker the amplification of a known fragment by the dilution PCR (FIG. 3). First, a $10^{-1}$ dilution series of the stock solution of the library is cultured, from which the plasmid is extracted for PCR. A liquid culture with a positive band at the lowest concentration is prepared in the same manner. The total volume of the dilution solution is divided into equal 10 portions, for culturing. In such manner, some of 10 test tubes contain the intended plasmid, while the remaining test tubes do not contain the plasmid. Because a 10-fold dilution of the liquid culture divided in such 10 portions has no positive band, theoretically, all the test tubes are never positive. The plasmid is extracted from the individual 10 test tubes, for PCR. A test tube with a positive band contains the target gene at a higher level than the level in the stock solution, because other portions with no content of the plasmid are preliminarily removed from the test tube. This procedure is repeatedly carried out to concentrate the target, so that only one plasmid can be screened. In such manner, a plasmid containing an insert of about 1.8 kbp was obtained. The nucleotide sequence of the fragment was determined. As a result of comparing with the cDNA sequence of Sasanishiki insofar determined, 99.5% homology was revealed. However, when the sequence was converted to amino acid sequence, it was shown that the sequence included a sequence of a 4-bp base inserted at a position in the sequence of Sasanishiki, which indicates that a frame shift occurred at the position. Excluding the position, the nucleotide sequence was converted to amino acid sequence. Then, it was shown that the resulting amino acid sequence had high homology to the amino acid sequence of the CPD photoreactivating enzyme of *Arabidopsis thaliana* (FIG. 8).

Using the Sasanishiki cDNA/pBS SK(-) library prepared from the Lamda ZAP II/rice cDNA library as template, further, screening was conducted by the above dilution PCR, for the cloning of a gene encoding a photoreactivating enzyme from Sasanishiki of the photoreactivation wild type. The resulting nucleotide sequence is shown as SEQ ID NO.2 (1521 base pairs), while the amino acid sequence of the protein encoded by the base pairs is shown as SEQ ID NO. 1 (the number of amino acid residues: 506).

(6) Verification of Photoreactivation Ability of CPD Photo-reactivating Enzyme Gene So as to further verify the photoreactivation ability of the CPD photoreactivating enzyme gene of Sasanishiki as recovered in accordance with the invention, additionally, the following experiment was carried out. First, NKJ3002 which is a deficient strain in all of the DNA repair abilities of *Escherichia coli* was prepared, followed by ultraviolet irradiation. Because NKJ3002 cannot repair DNA lesions such as CPD and 6-4 adduct generated by ultraviolet irradiation, the increase of the dose involves the decrease of the survival rate. Further, as the strain is also deficient in the photoreactivation gene of *Escherichia coli*, the irradiation of visible light after ultraviolet irradiation cannot cause any change, compared with no irradiation of visible light. A plasmid prepared for the expression of the CPD photoreactivating enzyme gene of Sasanishiki was introduced into the strain, for carrying out the same experiment. Consequently, it was observed that the survival rate was improved distinctly by the irradiation of visible light after ultraviolet irradiation. The CPD photoreactivating enzyme gene of Sasanishiki compensated the ultraviolet sensitivity of the photoreactivation gene-deficient *Escherichia coli*. In other words, it was absolutely verified that the product of the CPD photoreactivating enzyme gene of Sasanishiki (the photoreactivating enzyme in accordance with the invention) should absolutely have the photoreactivation ability.

INDUSTRIAL APPLICABILITY

As described above, *Oryza* includes ultraviolet resistant species (Sasanishiki) and ultraviolet sensitive species (Norin No.1) (6). The difference in photoreactivation activity between these two species considerably close to each other in terms of strain has not yet been elucidated. However, the Northern hybridization using the novel gene obtained in accordance with the invention and the cDNA fragment thereof enables the comparison in mRNA transcription level (enzyme expression level) between the CPD photoreactivating enzymes of the two species. Additionally, visible light irradiated after germination (leaf development) promotes the photoreactivation activity of *Oryza*. The activity reaches the maximum when the leaves completely develop. The induction of photoreactivation activity in photoenvironment differs depending on the plant. In case of *Oryza*, visible light elevates the induction as described above, while in case of *Arabidopsis thaliana*, even ultraviolet light can induce the activity. As described above, the induction of the photoreactivation activity of the plants in photoenvironment is largely not yet elucidated. It is expected that the Northern hybridization using the gene obtained at the present time and the cDNA fragment thereof in various photoenvironment at various growth stages will provide a clue for the elucidation of what kind of influences different photo-environment makes to the individual growth stages of *Oryza*.

Figure 10:
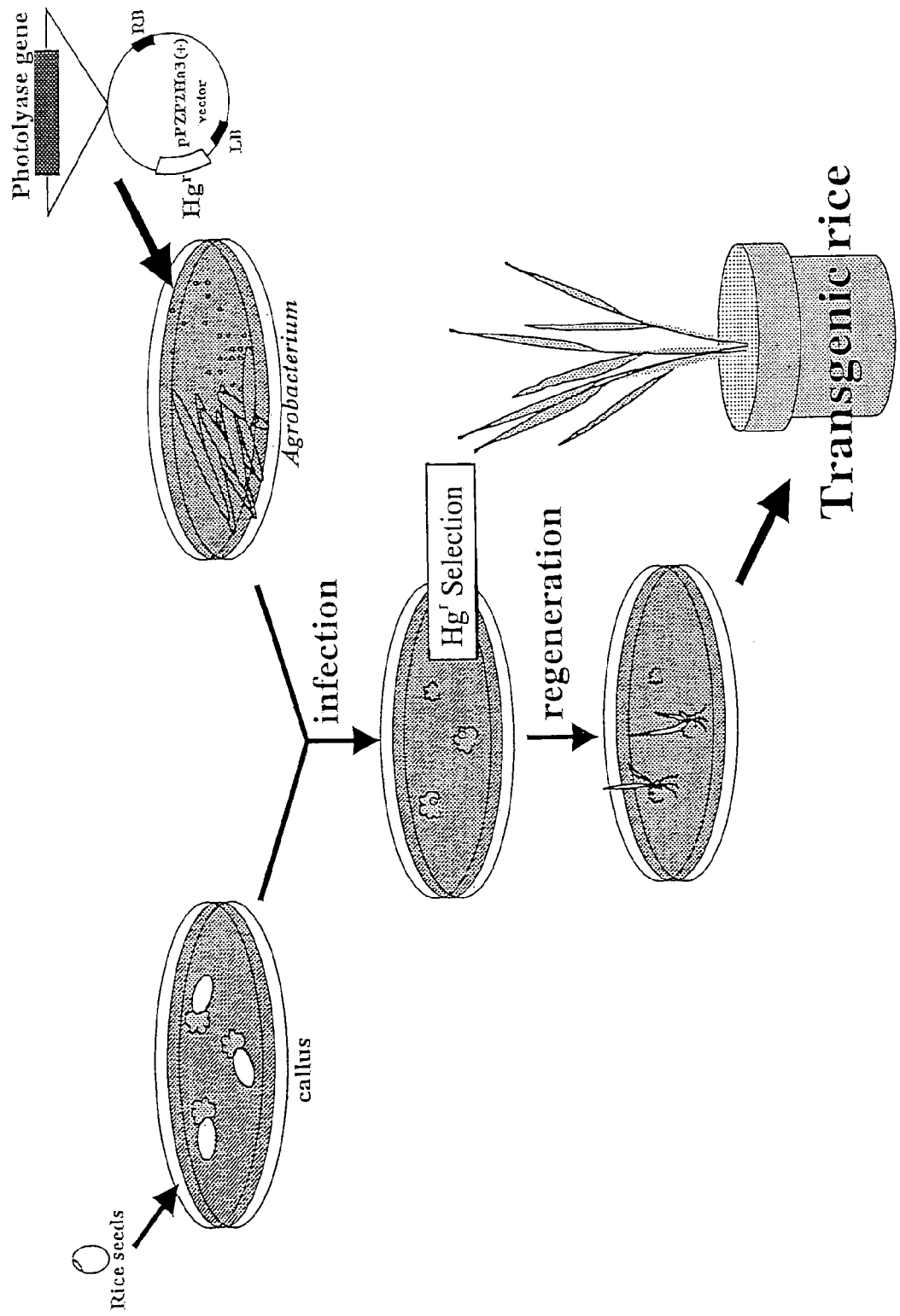
FIG. 10 is a schematic view showing the procedures for giving resistance to ultraviolet light to a species ultraviolet-sensitive or allowing a strain resistant to ultraviolet light to more highly express the CPD photoreactivating enzyme, through the introduction of the gene of the invention.

The gene obtained in accordance with the invention can be used further to carry out the complementarity test of *Escherichia coli* of a deficient type in photoreactivating enzyme, the crystallization of the enzyme, and the preparation of an antibody. Additionally, the distribution of a CPD photoreactivating enzyme in a plant cell can be observed by in situ hybridization with the antibody, to elucidate the involvement of the enzyme in DNA (mitochondria, chlorophyll) other than nucleus. By the gene introduction technology, additionally, ultraviolet resistance can be given to an ultraviolet sensitive species (for example, Norin No.1); the complementarity test can be carried out; or a species at the higher expression level of a CPD photoreactivating enzyme can be generated from an ultraviolet resistant strain (FIG. 10). The species at the higher level of the CPD photoreactivating enzyme will potentially be produced in a stable manner in the environment of an enormous dose of ultraviolet light due to a possible destruction of the ozone layer in future.

The invention claimed is:

1. An isolated DNA encoding a protein comprising the amino acid sequence of SEQ ID NO:1.

2. An isolated DNA including (a) or (b): (a) the nucleotide sequence represented by SEQ ID NO:2; (b) DNA with 95% or higher homology to the nucleotide sequence of (a), which encodes a protein with the activity of a CPD photoreactivating enzyme.

3. A recombinant expression vehicle carrying DNA according to any one of claims 1 or 2.

4. The recombinant expression vehicle according to claim 3, where the recombinant expression vehicle is lamda phage.

5. The recombinant expression vehicle according to claim 3, where the recombinant expression vehicle is a plasmid vector.

6. A transformant prepared by transformation with a recombinant expression vehicle carrying DNA according to any one of claims 1 or 2, wherein the transformant is a plant or *Escherichia coli*.

7. The transformant according to claim 6, where the transformant is a plant.

8. The transformant according to claim 6, where the transformant is from the genus *Oryza*.

9. The transformant according to claim 6, where the transformant is *Escherichia coli*.

* * * * *

SEQUENCE LISTING

<160> NUMBER OF SEQ ID NOS: 10

<210> SEQ ID NO 1
<211> LENGTH: 506
<212> TYPE: PRT
<213> ORGANISM: Oryza sativa

<400> SEQUENCE: 1

```
Met Pro Pro Thr Ser Val Ser Pro Pro Arg Thr Ala Pro Gly Pro Ala
 1               5                  10                  15

Asn Pro Ser Pro Ala His Pro Ser Arg Val Arg Val Ile His Pro Gly
             20                  25                  30

Gly Gly Lys Pro Gly Gly Pro Val Val Tyr Trp Met Leu Arg Asp Gln
         35                  40                  45

Arg Leu Ala Asp Asn Trp Ala Leu Leu His Ala Ala Gly Leu Ala Ala
     50                  55                  60

Ala Ser Ala Ser Pro Leu Ala Val Ala Phe Ala Leu Phe Pro Arg Pro
 65                  70                  75                  80

Phe Leu Leu Ser Ala Arg Arg Arg Gln Leu Gly Phe Leu Leu Arg Gly
                 85                  90                  95

Leu Arg Arg Leu Ala Ala Asp Ala Ala Ala Arg His Leu Pro Phe Phe
            100                 105                 110

Leu Phe Thr Gly Gly Pro Ala Glu Ile Pro Ala Leu Val Gln Arg Leu
        115                 120                 125

Gly Ala Ser Thr Leu Val Ala Asp Phe Ser Pro Leu Arg Pro Val Arg
    130                 135                 140

Glu Ala Leu Asp Ala Val Val Gly Asp Leu Arg Arg Glu Ala Pro Gly
145                 150                 155                 160
```

```
Val Ala Val His Gln Val Asp Ala His Asn Val Val Pro Val Trp Thr
            165                 170                 175

Ala Ser Ala Lys Met Glu Tyr Ser Ala Lys Thr Phe Arg Gly Lys Val
            180                 185                 190

Ser Lys Val Met Asp Glu Tyr Leu Val Glu Phe Pro Glu Leu Pro Ala
            195                 200                 205

Val Val Pro Trp Asp Arg Glu Gln Pro Glu Gly Val Asp Trp Asp Ala
            210                 215                 220

Leu Ile Ala Arg Val Cys Ser Glu Ala Glu Asn Val Pro Glu Ile Asp
225                 230                 235                 240

Trp Cys Glu Pro Gly Glu Ala Ala Ile Glu Ala Leu Leu Gly Ser
            245                 250                 255

Lys Asp Gly Phe Leu Thr Lys Arg Ile Lys Ser Tyr Glu Thr Asp Arg
            260                 265                 270

Asn Asp Pro Thr Lys Pro Arg Ala Leu Ser Gly Leu Ser Pro Tyr Leu
            275                 280                 285

His Phe Gly His Ile Ser Ala Gln Arg Cys Ala Leu Glu Ala Lys Lys
            290                 295                 300

Cys Arg His Leu Ser Pro Lys Ser Val Asp Ala Phe Leu Glu Glu Leu
305                 310                 315                 320

Val Val Arg Arg Glu Leu Ala Asp Asn Phe Cys Tyr Tyr Gln Pro Gln
            325                 330                 335

Tyr Asp Ser Leu Ser Gly Ala Trp Glu Trp Ala Arg Lys Thr Leu Met
            340                 345                 350

Asp His Ala Ala Asp Lys Arg Glu His Ile Tyr Thr Arg Glu Gln Leu
            355                 360                 365

Glu Asn Ala Lys Thr His Asp Pro Leu Trp Asn Ala Ser Gln Leu Glu
            370                 375                 380

Met Val His His Gly Glu Met His Gly Phe Met Arg Met Tyr Trp Ala
385                 390                 395                 400

Lys Lys Ile Leu Glu Trp Thr Ser Gly Pro Glu Glu Ala Leu Ser Thr
            405                 410                 415

Ala Ile Tyr Leu Asn Asp Lys Tyr Glu Ile Asp Gly Arg Asp Pro Ser
            420                 425                 430

Gly Tyr Val Gly Cys Met Trp Ser Ile Cys Gly Leu His Asp Gln Gly
            435                 440                 445

Trp Lys Glu Arg Pro Val Phe Gly Lys Ile Arg Tyr Met Asn Tyr Ala
450                 455                 460

Gly Cys Lys Arg Lys Phe Asp Val Asp Ala Tyr Ile Ser Tyr Val Lys
465                 470                 475                 480

Arg Leu Ala Gly Gln Ser Lys Lys Arg Asn Ala Glu Glu Ser Pro Asn
            485                 490                 495

Pro Val Val Lys Leu Ser Lys Ser Gln His
            500                 505

<210> SEQ ID NO 2
<211> LENGTH: 1521
<212> TYPE: DNA
<213> ORGANISM: Oryza sativa

<400> SEQUENCE: 2
atgccgccga cctcagtgag cccaccaaga acagcgccgg ggccggcgaa cccgagcccg      60 gcacaccegt cccgcgtgcg ggtgatccac ccgggcggcg ggaagcccgg tgggccggtg     120
gtgtactgga tgctgcggga ccagcggctc gccgacaact gggcgctcct ccacgccgcc     180
```

-continued

| | |
|---|---|
| ggcctcgccg ccgcctccgc gtccccgctc gccgtcgcgt tcgcgctgtt cccgaggccc | 240 |
| ttcctcctct ccgcccgccg ccgccagctc gggttcctcc tccgcggcct ccgccgcctc | 300 |
| gccgccgacg ccgccgcccg ccacctcccc ttcttcctct tcaccggtgg gcccgcggag | 360 |
| atcccggcgc tggtgcagcg ccttggtgcg tcgacgctgg tcgccgactt ctcgccgctg | 420 |
| cggccggtga gggaggcgct cgacgcgtg gtcggcgacc tgcggcggga ggcgcccggt | 480 |
| gtggccgtgc accaggtgga cgcgcacaac gtggtgcctg tgtggacggc gtcggcgaag | 540 |
| atggagtatt cagccaagac cttcagaggc aaggtgagca aggtgatgga tgagtacctt | 600 |
| gtggagttcc ctgaattgcc ggcggtggtg ccatgggaca gggagcagcc ggaggggtc | 660 |
| gactgggacg cactcatcgc cagggtttgc agtgaggcgg agaatgtgcc ggagattgac | 720 |
| tggtgtgagc ctggagagga agcagccata gaggcgcttc tcggcagcaa ggatggattc | 780 |
| ctgacgaaga ggatcaagag ctatgaaact gaccggaatg atcccacgaa accacgggca | 840 |
| ttgtctgggc tttcaccata ccttcatttt gggcacattt cggcacagcg gtgtgcgctc | 900 |
| gaggcaaaga aatgccgaca tcttagtccc aagtccgtcg atgctttctt ggaggaattg | 960 |
| gttgtaagga gggaattagc tgacaacttc tgctattacc aacctcaata tgattcgctg | 1020 |
| tctggtgcat gggaatgggc aaggaagaca ctgatggatc atgctgctga taaaagagag | 1080 |
| catatctata cgagggaaca gcttgagaat gccaaaacac atgatccttt gtggaatgca | 1140 |
| tcgcagttgg agatggttca ccatggagaa atgcatggat tcatgagaat gtactgggcc | 1200 |
| aaaaagattc tagaatggac tagtggacca agaagcac tttcaactgc aatttattta | 1260 |
| aatgacaagt atgagataga tgcagggac cccagtggtt acgtcggatg tatgtggtcc | 1320 |
| atatgtggcc tccatgatca gggttggaag gagcgtccag tatttggaaa gatacgttac | 1380 |
| atgaattacg ctggctgcaa gagaaaattc gatgttgacg cttacatttc ttatgtcaag | 1440 |
| agattagctg tcaatccaa gaagaggaac gctgaggagt ctccaaatcc tgtagtcaag | 1500 |
| ctttccaagt ctcagcacta a | 1521 |

<210> SEQ ID NO 3
<211> LENGTH: 496
<212> TYPE: PRT
<213> ORGANISM: Arabidopsis thaliana

<400> SEQUENCE: 3

Met Ala Ser Thr Val Ser Val Gln Pro Gly Arg Ile Arg Ile Leu Lys
 1               5                  10                  15

Lys Gly Ser Trp Gln Pro Ser Asp Gln Thr Val Gly Pro Val Val Tyr
            20                  25                  30

Trp Met Phe Arg Asp Gln Arg Leu Lys Asp Asn Trp Ala Leu Ile His
        35                  40                  45

Ala Val Asp Leu Ala Asn Arg Thr Asn Ala Pro Val Ala Val Val Phe
    50                  55                  60

Asn Leu Phe Asp Gln Phe Leu Asp Ala Lys Ala Arg Gln Leu Gly Phe
65                  70                  75                  80

Met Leu Lys Gly Leu Arg Gln Leu His His Gln Ile Asp Ser Leu Gln
                85                  90                  95

Ile Pro Phe Phe Leu Leu Gln Gly Asp Ala Lys Glu Thr Ile Pro Asn
            100                 105                 110

Phe Leu Thr Glu Cys Gly Ala Ser His Leu Val Thr Asp Phe Ser Pro
        115                 120                 125

-continued

```
Leu Arg Glu Ile Arg Arg Cys Lys Asp Glu Val Val Lys Arg Thr Ser
    130                 135                 140

Asp Ser Leu Ala Ile His Glu Val Asp Ala His Asn Val Val Pro Met
145                 150                 155                 160

Trp Ala Ala Ser Ser Lys Leu Glu Tyr Ser Ala Arg Thr Ile Arg Gly
                165                 170                 175

Lys Ile Asn Lys Leu Leu Pro Asp Tyr Leu Ile Glu Phe Pro Lys Leu
            180                 185                 190

Glu Pro Pro Lys Lys Lys Trp Thr Gly Met Met Asp Lys Lys Leu Val
        195                 200                 205

Asp Trp Asp Ser Leu Ile Asp Lys Val Val Arg Glu Gly Ala Glu Val
    210                 215                 220

Pro Glu Ile Glu Trp Cys Val Pro Gly Glu Asp Ala Gly Ile Glu Val
225                 230                 235                 240

Leu Met Gly Asn Lys Asp Gly Phe Leu Thr Lys Arg Leu Lys Asn Tyr
                245                 250                 255

Ser Thr Asp Arg Asn Asn Pro Ile Lys Pro Lys Ala Leu Ser Gly Leu
            260                 265                 270

Ser Pro Tyr Leu His Phe Gly Gln Val Ser Ala Gln Arg Cys Ala Leu
        275                 280                 285

Glu Ala Arg Lys Val Arg Ser Thr Ser Pro Gln Ala Val Asp Ile Phe
    290                 295                 300

Leu Glu Glu Leu Ile Val Arg Arg Glu Leu Ser Asp Asn Phe Cys Tyr
305                 310                 315                 320

Tyr Gln Pro His Tyr Asp Ser Leu Lys Gly Ala Trp Glu Trp Ala Arg
                325                 330                 335

Lys Ser Leu Met Asp His Ala Ser Asp Lys Arg Glu His Ile Tyr Ser
            340                 345                 350

Leu Glu Gln Leu Glu Lys Gly Leu Thr Ala Asp Pro Leu Trp Asn Ala
        355                 360                 365

Ser Gln Leu Glu Met Leu Tyr Gln Gly Lys Met His Gly Phe Met Arg
    370                 375                 380

Met Tyr Trp Ala Lys Lys Ile Leu Glu Trp Thr Lys Gly Pro Glu Glu
385                 390                 395                 400

Ala Leu Ser Ile Ser Ile Tyr Leu Asn Asn Lys Tyr Glu Ile Asp Gly
                405                 410                 415

Arg Asp Pro Ser Gly Tyr Val Gly Cys Met Trp Ser Ile Cys Gly Val
            420                 425                 430

His Asp Gln Gly Trp Lys Glu Arg Pro Val Phe Gly Lys Ile Arg Tyr
        435                 440                 445

Met Asn Tyr Ala Gly Cys Lys Arg Lys Phe Asn Val Asp Ser Tyr Ile
    450                 455                 460

Ser Tyr Val Lys Ser Leu Val Ser Val Thr Lys Lys Arg Lys Ala
465                 470                 475                 480

Glu Glu Gln Leu Thr Arg Asp Ser Val Asp Pro Lys Ile Thr Ile Val
                485                 490                 495

<210> SEQ ID NO 4
<211> LENGTH: 612
<212> TYPE: PRT
<213> ORGANISM: Chlamydomonas reinhardtii

<400> SEQUENCE: 4

Met Ser Ser Lys Arg Lys Ala Thr Glu Ala Pro Ala Ala Gly Glu Asp
1               5                   10                  15
```

-continued

```
Gly Ala Ala Gly Pro Ser Ser Lys Lys Gln Ala Ala Ser Ala Ser
                 20                  25                  30
Ala Ala Ala Ala Ala Ala Gly Ala Gly Ser Ala Ala Gly Gly Ala
             35                  40                  45
Leu Val Asn Pro Lys Arg Val Arg Val Leu Lys Pro Gly Ser Ile Gly
         50                  55                  60
Lys Gly Pro Val Val Tyr Trp Met Ser Arg Asp Gln Arg Leu Ala Asp
 65                  70                  75                  80
Asn Trp Ala Leu Leu His Ala Ile Glu Ala Gln Gly Ala Ala Gly
                 85                  90                  95
Ser Ser Gln Val Ala Val Ala Phe Asn Leu Val Pro Ala Phe Leu Gly
                100                 105                 110
Ala Gly Ala Arg Gln Phe Gly Phe Met Leu Arg Gly Leu Arg Gln Leu
            115                 120                 125
Ala Pro Arg Leu Glu Ala Arg Gly Ile Lys Phe Tyr Leu Leu Lys Gly
        130                 135                 140
Asp Pro Ala His Thr Leu Pro Gln Leu Val Ser Gly Leu Gly Ala Gly
145                 150                 155                 160
Leu Leu Val Thr Asp Tyr Ser Pro Leu Arg Leu Gly Arg Thr Trp Arg
                165                 170                 175
Asp Gln Val Cys Ser Ala Leu Gly Ser Val Pro Val His Glu Val Asp
            180                 185                 190
Ala His Asn Val Val Pro Val Trp Ala Ala Ser Glu Lys Arg Glu Val
        195                 200                 205
Gly Ala Arg Thr Leu Arg Pro Lys Ile His Lys Ala Leu Pro Glu Phe
    210                 215                 220
Leu Arg Glu Phe Pro Glu Val Pro Thr Leu Pro Ala Trp Thr Pro Ala
225                 230                 235                 240
Val Ala Pro Glu Ala Val Asp Trp Asp Gly Leu Ile Ser Glu Val Leu
                245                 250                 255
Ser Arg Gly Ala Asp Val Pro Glu Val Glu Trp Cys Thr Pro Gly Glu
            260                 265                 270
Glu Ala Ala Leu Glu Ala Leu Thr Gly Pro Arg Gly Phe Leu Ser Pro
        275                 280                 285
Ala Arg Leu Ser Leu Tyr Asp Thr Lys Arg Asn Asp Pro Ala Thr Pro
    290                 295                 300
Ser Ala Leu Ser Gly Leu Ser Pro Tyr Leu His Phe Gly Gln Leu Ala
305                 310                 315                 320
Pro Gln Arg Ala Ala Leu Glu Ala Ala Lys His Arg Ala Lys Tyr Lys
                325                 330                 335
Ala Ala Val Glu Ser Tyr Leu Glu Glu Leu Val Val Arg Arg Glu Leu
            340                 345                 350
Ala Asp Asn Phe Cys His Tyr Cys Pro Thr Tyr Asp Ser Leu Glu Ala
        355                 360                 365
Ala Ala Glu Trp Ala Arg Asp Ser Leu Asp Lys His Arg Thr Asp Lys
    370                 375                 380
Arg Glu Phe Leu Tyr Thr Arg Asp Gln Leu Glu Cys Gly Ala Thr His
385                 390                 395                 400
Asp Glu Leu Trp Asn Ala Ala Gln Leu Glu Met Val His Val Gly Lys
                405                 410                 415
Met His Gly Phe Met Arg Met Tyr Trp Ala Lys Lys Ile Leu Glu Trp
            420                 425                 430
```

```
Thr Gln Gly Pro Glu Gln Ala Ile Glu Trp Ala Ile Tyr Leu Asn Asp
        435                 440                 445

Arg Tyr Glu Leu Asp Gly Arg Asp Pro Gly Gly Tyr Thr Gly Val Leu
        450                 455                 460

Trp Ser Met Ala Gly Val His Asp Met Gly Trp Ala Glu Arg Ala Val
465                 470                 475                 480

Phe Gly Lys Ile Arg Tyr Met Asn Tyr Asn Gly Cys Lys Arg Lys Phe
            485                 490                 495

Asp Ile Lys Ala Tyr Val Ala Tyr Val Ser Lys Ala Val Ala Glu Ala
                500                 505                 510

Lys Ala Lys Gly Arg Ala Ala Lys Leu Pro Ser Ala Ala Ala Ala Gly
            515                 520                 525

Ala Ser Gly Ala Ala Ala Gly Ala Thr Ala Ala Ala Ala Ala Ala Ala
        530                 535                 540

Ala Ala Pro Gly Pro Ser Gly Ala Gln Ala Ala Lys Ala Ala Lys Ala
545                 550                 555                 560

Lys Ala Glu Pro Lys Glu Ala Lys Pro Lys Ala Ala Lys Ala Ala Ala
            565                 570                 575

Lys Ala Lys Gly Pro Lys Asp Glu Lys Ala Ala Ala Gly Ala Lys
            580                 585                 590

Arg Lys Ala Ala Lys Pro Ala Lys Ser Ala Ser Ser Gly Glu Glu Gly
        595                 600                 605

Ser Asp Asp Glu
        610

<210> SEQ ID NO 5
<211> LENGTH: 137
<212> TYPE: PRT
<213> ORGANISM: Oryza sativa

<400> SEQUENCE: 5

Val Trp Thr Ala Ser Ala Lys Met Glu Tyr Ser Ala Lys Thr Phe Arg
  1               5                  10                  15

Gly Lys Val Ser Lys Val Met Asp Glu Tyr Leu Val Glu Phe Pro Glu
                20                  25                  30

Leu Pro Ala Val Val Pro Trp Asp Arg Glu Gln Pro Glu Gly Val Asp
            35                  40                  45

Trp Asp Ala Leu Ile Ala Arg Val Cys Arg Cys Gly Gln Ser Val Asp
     50                  55                  60

Ala Phe Leu Glu Glu Leu Val Val Arg Arg Glu Leu Ala Asp Asn Phe
 65                  70                  75                  80

Cys Tyr Tyr Gln Pro Gln Tyr Asp Ser Leu Ser Gly Ala Trp Glu Trp
                85                  90                  95

Ala Arg Lys Thr Leu Met Asp His Ala Ala Asp Lys Arg Glu His Ile
                100                 105                 110

Tyr Thr Asn Asp Tyr Gln Leu Trp Asn Ala Ser Gln Leu Glu Met Val
            115                 120                 125

His His Gly Lys Met His Gly Phe Met
        130                 135

<210> SEQ ID NO 6
<211> LENGTH: 263
<212> TYPE: PRT
<213> ORGANISM: Arabidopsis thaliana

<400> SEQUENCE: 6
```

His Leu Val Thr Asp Phe Ser Pro Leu Arg Glu Ile Arg Arg Cys Lys
1               5                   10                  15

Asp Glu Val Val Lys Arg Thr Ser Asp Ser Leu Ala Ile His Glu Val
                20                  25                  30

Asp Ala His Asn Val Val Pro Met Trp Ala Ala Ser Ser Lys Leu Glu
            35                  40                  45

Tyr Ser Ala Arg Thr Ile Arg Gly Lys Ile Asn Lys Leu Leu Pro Asp
        50                  55                  60

Tyr Leu Ile Glu Phe Pro Lys Leu Glu Pro Pro Lys Lys Lys Trp Thr
65                  70                  75                  80

Gly Met Met Asp Lys Lys Leu Val Asp Trp Asp Ser Leu Ile Asp Lys
                85                  90                  95

Val Val Arg Glu Gly Ala Glu Val Pro Glu Ile Glu Trp Cys Val Pro
                100                 105                 110

Gly Glu Asp Ala Gly Ile Glu Val Leu Met Gly Asn Lys Asp Gly Phe
            115                 120                 125

Leu Thr Lys Arg Leu Lys Asn Tyr Ser Thr Asp Arg Asn Asn Pro Ile
        130                 135                 140

Lys Pro Lys Ala Leu Ser Gly Leu Ser Pro Tyr Leu His Phe Gly Gln
145                 150                 155                 160

Val Ser Ala Gln Arg Cys Ala Leu Glu Ala Arg Lys Val Arg Ser Thr
                165                 170                 175

Ser Pro Gln Ala Val Asp Ile Phe Leu Glu Glu Leu Ile Val Arg Arg
            180                 185                 190

Glu Leu Ser Asp Asn Phe Cys Tyr Tyr Gln Pro His Tyr Asp Ser Leu
        195                 200                 205

Lys Gly Ala Trp Glu Trp Ala Arg Lys Ser Leu Met Asp His Ala Ser
210                 215                 220

Asp Lys Arg Glu His Ile Tyr Ser Leu Glu Gln Leu Glu Lys Gly Leu
225                 230                 235                 240

Thr Ala Asp Pro Leu Trp Asn Ala Ser Gln Leu Glu Met Leu Tyr Gln
                245                 250                 255

Gly Lys Met His Gly Phe Met
            260

<210> SEQ ID NO 7
<211> LENGTH: 333
<212> TYPE: PRT
<213> ORGANISM: Oryza sativa

<400> SEQUENCE: 7

Val Trp Thr Ala Ser Ala Lys Met Glu Tyr Ser Ala Lys Thr Phe Arg
1               5                   10                  15

Gly Lys Val Ser Lys Val Met Asp Glu Tyr Leu Val Glu Phe Pro Glu
                20                  25                  30

Leu Pro Ala Val Val Pro Trp Asp Arg Glu Gln Pro Glu Gly Val Asp
            35                  40                  45

Trp Asp Ala Leu Ile Ala Arg Val Cys Ser Glu Ala Glu Asn Val Pro
        50                  55                  60

Glu Ile Asp Trp Cys Glu Pro Gly Glu Glu Ala Ala Ile Glu Ala Leu
65                  70                  75                  80

Leu Gly Ser Lys Asp Gly Phe Leu Thr Lys Arg Ile Lys Ser Tyr Glu
                85                  90                  95

Thr Asp Arg Asn Asp Pro Thr Lys Pro Arg Ala Leu Ser Gly Leu Ser
                100                 105                 110

```
Pro Tyr Leu His Phe Gly His Ile Ser Ala Gln Arg Cys Ala Leu Glu
            115                 120                 125

Ala Lys Lys Cys Arg His Leu Ser Pro Lys Ser Val Asp Ala Phe Leu
    130                 135                 140

Glu Glu Leu Val Val Arg Arg Glu Leu Ala Asp Asn Phe Cys Tyr Tyr
145                 150                 155                 160

Gln Pro Gln Tyr Asp Ser Leu Ser Gly Ala Trp Glu Trp Ala Arg Lys
                165                 170                 175

Thr Leu Met Asp His Ala Ala Asp Lys Arg Glu His Ile Tyr Thr Arg
            180                 185                 190

Glu Gln Leu Glu Asn Ala Lys Thr His Asp Pro Leu Trp Asn Ala Ser
        195                 200                 205

Gln Leu Glu Met Val His His Gly Lys Met His Gly Phe Met Arg Met
    210                 215                 220

Tyr Trp Ala Lys Lys Ile Leu Glu Trp Thr Ser Gly Pro Glu Glu Ala
225                 230                 235                 240

Leu Ser Thr Ala Ile Tyr Leu Asn Asp Lys Tyr Glu Ile Asp Gly Arg
                245                 250                 255

Asp Pro Ser Gly Tyr Val Gly Cys Met Trp Ser Ile Cys Gly Leu His
            260                 265                 270

Asp Gln Gly Trp Lys Glu Arg Pro Val Phe Gly Lys Ile Arg Tyr Met
        275                 280                 285

Asn Tyr Ala Gly Cys Lys Arg Lys Phe Asp Val Asp Ala Tyr Ile Ser
    290                 295                 300

Tyr Val Lys Arg Leu Ala Gly Gln Ser Lys Lys Arg Asn Ala Glu Glu
305                 310                 315                 320

Ser Pro Asn Pro Val Lys Leu Ser Lys Ser Gln His
                325                 330

<210> SEQ ID NO 8
<211> LENGTH: 376
<212> TYPE: PRT
<213> ORGANISM: Arabidopsis thaliana

<400> SEQUENCE: 8

His Leu Val Thr Asp Phe Ser Pro Leu Arg Glu Ile Arg Arg Cys Lys
1               5                   10                  15

Asp Glu Val Val Lys Arg Thr Ser Asp Ser Leu Ala Ile His Glu Val
            20                  25                  30

Asp Ala His Asn Val Val Pro Met Trp Ala Ala Ser Ser Lys Leu Glu
        35                  40                  45

Tyr Ser Ala Arg Thr Ile Arg Gly Lys Ile Asn Lys Leu Leu Pro Asp
    50                  55                  60

Tyr Leu Ile Glu Phe Pro Lys Leu Glu Pro Pro Lys Lys Lys Trp Thr
65                  70                  75                  80

Gly Met Met Asp Lys Lys Leu Val Asp Trp Asp Ser Leu Ile Asp Lys
                85                  90                  95

Val Val Arg Glu Gly Ala Glu Val Pro Glu Ile Glu Trp Cys Val Pro
            100                 105                 110

Gly Glu Asp Ala Gly Ile Glu Val Leu Met Gly Asn Lys Asp Gly Phe
        115                 120                 125

Leu Thr Lys Arg Leu Lys Asn Tyr Ser Thr Asp Arg Asn Asn Pro Ile
    130                 135                 140

Lys Pro Lys Ala Leu Ser Gly Leu Ser Pro Tyr Leu His Phe Gly Gln
```

```
145                 150                 155                 160
Val Ser Ala Gln Arg Cys Ala Leu Glu Ala Arg Lys Val Arg Ser Thr
                165                 170                 175

Ser Pro Gln Ala Val Asp Ile Phe Leu Glu Glu Leu Ile Val Arg Arg
            180                 185                 190

Glu Leu Ser Asp Asn Phe Cys Tyr Tyr Gln Pro His Tyr Asp Ser Leu
            195                 200                 205

Lys Gly Ala Trp Glu Trp Ala Arg Lys Ser Leu Met Asp His Ala Ser
        210                 215                 220

Asp Lys Arg Glu His Ile Tyr Ser Leu Glu Gln Leu Glu Lys Gly Leu
225                 230                 235                 240

Thr Ala Asp Pro Leu Trp Asn Ala Ser Gln Leu Glu Met Leu Tyr Gln
                245                 250                 255

Gly Lys Met His Gly Phe Met Arg Met Tyr Trp Ala Lys Lys Ile Leu
            260                 265                 270

Glu Trp Thr Lys Gly Pro Glu Ala Leu Ser Ile Ser Ile Tyr Leu
        275                 280                 285

Asn Asn Lys Tyr Glu Ile Asp Gly Arg Asp Pro Ser Gly Tyr Val Gly
290                 295                 300

Cys Met Trp Ser Ile Cys Gly Val His Asp Gln Gly Trp Lys Glu Arg
305                 310                 315                 320

Pro Val Phe Gly Lys Ile Arg Tyr Met Asn Tyr Ala Gly Cys Lys Arg
                325                 330                 335

Lys Phe Asn Val Asp Ser Tyr Ile Ser Tyr Val Lys Ser Leu Val Ser
            340                 345                 350

Val Thr Lys Lys Arg Lys Ala Glu Glu Gln Leu Thr Arg Asp Ser
        355                 360                 365

Val Asp Pro Lys Ile Thr Ile Val
370                 375

<210> SEQ ID NO 9
<211> LENGTH: 480
<212> TYPE: PRT
<213> ORGANISM: Oryza sativa

<400> SEQUENCE: 9

Met Pro Pro Thr Ser Val Ser Pro Pro Arg Thr Ala Pro Gly Pro Ala
 1               5                  10                  15

Asn Pro Ser Pro Ala His Pro Ser Arg Val Arg Val Ile His Pro Gly
            20                  25                  30

Gly Gly Lys Pro Gly Gly Pro Val Val Tyr Trp Met Leu Arg Asp Arg
        35                  40                  45

Leu Ala Asp Asn Trp Ala Leu Leu His Ala Ala Gly Leu Ala Ala Ala
    50                  55                  60

Ser Ala Ser Pro Leu Ala Val Ala Phe Ala Leu Phe Pro Arg Pro Phe
65                  70                  75                  80

Leu Leu Ser Ala Arg Arg Gln Leu Gly Phe Leu Leu Arg Gly Leu
                85                  90                  95

Arg Arg Leu Ala Ala Asp Ala Ala Arg His Leu Pro Phe Phe Leu
            100                 105                 110

Phe Thr Gly Gly Pro Ala Glu Ile Pro Ala Leu Val Arg Arg Leu Gly
        115                 120                 125

Ala Ser Thr Leu Val Ala Asp Phe Ser Pro Leu Arg Pro Val Arg Glu
    130                 135                 140
```

```
Ala Leu Asp Ala Val Val Gly Asp Leu Arg Arg Glu Ala Pro Gly Val
145                 150                 155                 160

Ala Val His Gln Val Asp Ala His Asn Val Val Pro Val Trp Thr Ala
            165                 170                 175

Ser Ala Lys Met Glu Tyr Ser Ala Lys Thr Phe Arg Gly Lys Val Ser
        180                 185                 190

Lys Val Met Asp Glu Tyr Leu Val Glu Phe Pro Glu Leu Pro Ala Val
    195                 200                 205

Val Pro Trp Asp Arg Glu Gln Pro Glu Gly Val Asp Trp Asp Ala Leu
    210                 215                 220

Ile Ala Arg Val Cys Ser Glu Ala Glu Asn Val Pro Glu Ile Asp Trp
225                 230                 235                 240

Cys Glu Pro Gly Glu Glu Ala Ala Ile Glu Ala Leu Leu Ser Ser Lys
                245                 250                 255

Asp Gly Phe Leu Thr Lys Arg Ile Lys Ser Tyr Glu Thr Asp Arg Asn
            260                 265                 270

Asp Pro Thr Lys Pro Arg Ala Leu Ser Gly Leu Ser Pro Tyr Leu His
        275                 280                 285

Phe Gly His Ile Ser Ala His Arg Cys Ala Leu Glu Ala Lys Lys Cys
    290                 295                 300

Arg His Leu Ser Pro Lys Ser Val Asp Ala Phe Leu Glu Glu Leu Val
305                 310                 315                 320

Val Arg Arg Glu Leu Ala Asp Asn Phe Cys Tyr Tyr Gln Pro Gln Tyr
                325                 330                 335

Asp Ser Leu Ser Gly Ala Trp Glu Trp Ala Arg Lys Thr Leu Met Asp
            340                 345                 350

His Ala Ala Asp Lys Arg Glu His Ile Tyr Thr Arg Glu Gln Leu Glu
        355                 360                 365

Asn Ala Lys Thr His Asp Pro Leu Trp Asn Ala Ser Gln Leu Glu Met
    370                 375                 380

Val His His Gly Lys Met His Gly Phe Met Arg Met Tyr Trp Ala Lys
385                 390                 395                 400

Lys Ile Leu Glu Trp Thr Ser Gly Pro Glu Glu Ala Leu Ser Thr Ala
                405                 410                 415

Ile Tyr Leu Asn Asp Lys Tyr Glu Ile Asp Gly Arg Asp Pro Ser Gly
            420                 425                 430

Tyr Val Gly Cys Met Trp Ser Ile Cys Gly Leu His Asp Gln Gly Trp
        435                 440                 445

Lys Glu Arg Pro Val Phe Gly Lys Ile Arg Tyr Met Asn Tyr Ala Gly
    450                 455                 460

Cys Lys Arg Lys Phe Asp Val Asp Ala Ser Phe Leu Met Ser Arg Asp
465                 470                 475                 480

<210> SEQ ID NO 10
<211> LENGTH: 496
<212> TYPE: PRT
<213> ORGANISM: Arabidopsis thaliana

<400> SEQUENCE: 10

Met Ala Ser Thr Val Ser Val Gln Pro Gly Arg Ile Arg Ile Leu Lys
1               5                   10                  15

Lys Gly Ser Trp Gln Pro Ser Asp Gln Thr Val Gly Pro Val Val Tyr
            20                  25                  30

Trp Met Phe Arg Asp Gln Arg Leu Lys Asp Asn Trp Ala Leu Ile His
        35                  40                  45
```

```
Ala Val Asp Leu Ala Asn Arg Thr Asn Ala Pro Val Ala Val Phe
     50                  55                  60

Asn Leu Phe Asp Gln Phe Leu Asp Ala Lys Ala Arg Gln Leu Gly Phe
 65              70                  75                      80

Met Leu Lys Gly Leu Arg Gln Leu His His Gln Ile Asp Ser Leu Gln
                 85                  90                  95

Ile Pro Phe Phe Leu Leu Gln Gly Asp Ala Lys Glu Thr Ile Pro Asn
                100                 105                110

Phe Leu Thr Glu Cys Gly Ala Ser His Leu Val Thr Asp Phe Ser Pro
            115                 120                 125

Leu Arg Glu Ile Arg Arg Cys Lys Asp Glu Val Val Lys Arg Thr Ser
    130                 135                 140

Asp Ser Leu Ala Ile His Glu Val Asp Ala His Asn Val Val Pro Met
145                 150                 155                 160

Trp Ala Ser Ser Lys Leu Glu Tyr Ser Ala Arg Thr Ile Arg Gly
                165                 170                 175

Lys Ile Asn Lys Leu Leu Pro Asp Tyr Leu Ile Glu Phe Pro Lys Leu
                180                 185                 190

Glu Pro Pro Lys Lys Lys Trp Thr Gly Met Met Asp Lys Lys Leu Val
        195                 200                 205

Asp Trp Asp Ser Leu Ile Asp Lys Val Val Arg Glu Gly Ala Glu Val
210                 215                 220

Pro Glu Ile Glu Trp Cys Val Pro Gly Glu Asp Ala Gly Ile Glu Val
225                 230                 235                 240

Leu Met Gly Asn Lys Asp Gly Phe Leu Thr Lys Arg Leu Lys Asn Tyr
                245                 250                 255

Ser Thr Asp Arg Asn Asn Pro Ile Lys Pro Lys Ala Leu Ser Gly Leu
            260                 265                 270

Ser Pro Tyr Leu His Phe Gly Gln Val Ser Ala Gln Arg Cys Ala Leu
        275                 280                 285

Glu Ala Arg Lys Val Arg Ser Thr Ser Pro Gln Ala Val Asp Ile Phe
290                 295                 300

Leu Glu Glu Leu Ile Val Arg Arg Glu Leu Ser Asp Asn Phe Cys Tyr
305                 310                 315                 320

Tyr Gln Pro His Tyr Asp Ser Leu Lys Gly Ala Trp Glu Trp Ala Arg
                325                 330                 335

Lys Ser Leu Met Asp His Ala Ser Asp Lys Arg Glu His Ile Tyr Ser
            340                 345                 350

Leu Glu Gln Leu Glu Lys Gly Leu Thr Ala Asp Pro Leu Trp Asn Ala
        355                 360                 365

Ser Gln Leu Glu Met Leu Tyr Gln Gly Lys Met His Gly Phe Met Arg
        370                 375                 380

Met Tyr Trp Ala Lys Lys Ile Leu Glu Trp Thr Lys Gly Pro Glu Glu
385                 390                 395                 400

Ala Leu Ser Ile Ser Ile Tyr Leu Asn Asn Lys Tyr Glu Ile Asp Gly
                405                 410                 415

Arg Asp Pro Ser Gly Tyr Val Gly Cys Met Trp Ser Ile Cys Gly Val
            420                 425                 430

His Asp Gln Gly Trp Lys Glu Arg Pro Val Phe Gly Lys Ile Arg Tyr
        435                 440                 445

Met Asn Tyr Ala Gly Cys Lys Arg Lys Phe Asn Val Asp Ser Tyr Ile
450                 455                 460
```

```
-continued

Ser Tyr Val Lys Ser Leu Val Ser Val Thr Lys Lys Lys Arg Lys Ala
465                 470                 475                 480

Glu Glu Gln Leu Thr Arg Asp Ser Val Asp Pro Lys Ile Thr Ile Val
                485                 490                 495
```